US008871264B2

(12) United States Patent
Hallgren et al.

(10) Patent No.: US 8,871,264 B2
(45) Date of Patent: Oct. 28, 2014

(54) IMMEDIATE RELEASE TABLET FORMULATIONS

(75) Inventors: Agneta Hallgren, Molndal (SE); Ralf Magnus Werner Swenson, Molndal (SE)

(73) Assignee: AstraZeneca AB, Sodertalje (SE)

( * ) Notice: Subject to any disclaimer, the term of this patent is extended or adjusted under 35 U.S.C. 154(b) by 103 days.

(21) Appl. No.: 13/509,213

(22) PCT Filed: Nov. 12, 2010

(86) PCT No.: PCT/US2010/056577
§ 371 (c)(1),
(2), (4) Date: Oct. 12, 2012

(87) PCT Pub. No.: WO2011/060290
PCT Pub. Date: May 19, 2011

(65) Prior Publication Data
US 2013/0034606 A1    Feb. 7, 2013

Related U.S. Application Data

(60) Provisional application No. 61/261,173, filed on Nov. 13, 2009.

(51) Int. Cl.
| | |
|---|---|
| *A61K 9/20* | (2006.01) |
| *A61K 9/28* | (2006.01) |
| *A61K 9/30* | (2006.01) |
| *A61K 31/70* | (2006.01) |
| *A61K 31/155* | (2006.01) |
| *A61K 45/06* | (2006.01) |
| *A61K 31/351* | (2006.01) |
| *A61K 9/24* | (2006.01) |

(52) U.S. Cl.
CPC ............. *A61K 9/2054* (2013.01); *A61K 31/155* (2013.01); *A61K 45/06* (2013.01); *A61K 9/209* (2013.01); *A61K 31/351* (2013.01)
USPC .......... 424/464; 424/475; 424/474; 427/2.14; 514/23; 514/635

(58) Field of Classification Search
USPC ............ 424/475, 474, 464; 427/2.14; 514/23, 514/635, 460
See application file for complete search history.

(56) References Cited

U.S. PATENT DOCUMENTS 5,955,106 A    9/1999    Moeckel
6,117,451 A    9/2000    Kumar
(Continued)

FOREIGN PATENT DOCUMENTS

| WO | WO 2005/117841 A1 | 12/2005 |
| WO | WO 2008/116179 A1 | 9/2008 |
| WO | WO 2010/045656 A2 | 4/2010 |

OTHER PUBLICATIONS

Anonymous ("View of NCT01002807 on Oct. 26, 2009," ClinicalTrials.gov archive (Oct. 26, 2009), pp. 1-3, retrieved from the internet: URL:http://clinicaltrials.gov/archive/NCT01002807/2009_10_26.).*

(Continued)

Primary Examiner — Blessing M Fubara
(74) Attorney, Agent, or Firm — Terence J. Bogie

(57) ABSTRACT

The present invention provides an immediate release pharmaceutical formulation which includes a tablet or capsule formulation comprising metformin and the sodium dependent glucose transporter (SGLT2) inhibitor dapagliflozin or its propylene glycol hydrate. The present invention also provides methods of preparing the formulations and methods of treating diseases or disorders associated with SGLT2 activity employing these formulations.

23 Claims, 3 Drawing Sheets

(56) References Cited

U.S. PATENT DOCUMENTS

| | | |
|---|---|---|
| 7,214,387 B2 | 5/2007 | Sanghvi |
| 8,535,715 B2 * | 9/2013 | Abebe et al. .................. 424/465 |
| 2008/0234366 A1 * | 9/2008 | Bindra et al. ................. 514/460 |

OTHER PUBLICATIONS

Anonymous: "View of NCT01002807 on Oct. 26, 2009," ClinicalTrials.gov archive (Oct. 26, 2009), pp. 1-3, retrieved from the internet: URL:http://clinicaltrials.gov/archive/NCTO1002807/2009_10_26.

Kukkar, Vipin et al.: "Mixing and formulation of low dose drugs: underlying problems and solutions," THAI Journal of Pharmaceutical Sciences, (Dec. 31, 2008) vol. 32, No. 3-4, pp. 43-58.

Mandal et al., "Formulation and In Vitro Studies of a Fixed-Dose Combination of a Bilayer Matrix Tablet Containing Metformin HCl as Sustained Release and Glipizide as Immediate Release," Drug Development and Industrial Pharmacy, 34:305-313, 2008.

\* cited by examiner

IMMEDIATE RELEASE TABLET FORMULATIONS

CROSS-REFERENCE TO RELATED APPLICATION

This application claims the benefit of International Application No. PCT/US2010/056577, filed Nov. 12, 2010, which claims the benefit of U.S. Provisional Application Ser. No. 61/261,173, filed on Nov. 13, 2009. The entire teachings of the referenced applications are herein incorporated by reference in their entirety.

FIELD OF THE INVENTION

The present invention provides an immediate release pharmaceutical formulation which includes a tablet or capsule formulation comprising metformin, a sodium dependent glucose transporter inhibitor (SGLT2), and optionally a coating. The present invention also provides methods of preparing the formulations and methods of treating diseases or disorders associated with SGLT2 activity employing these formulations.

BACKGROUND OF THE INVENTION

Type II diabetes is the most common form of diabetes accounting for 90% of diabetes cases. Over 100 million people worldwide have type-2 diabetes (nearly 17 million in the U.S.) and the prevalence is increasing dramatically in both the developed and developing worlds. Type-II diabetes is a lifelong illness, which generally starts in middle age or later part of life, but can start at any age. Patients with type-2 diabetes do not respond properly to insulin, the hormone that normally allows the body to convert blood glucose into energy or store it in cells to be used later. The problem in type-2 diabetes is a condition called insulin resistance where the body produces insulin, in normal or even high amounts, but certain mechanisms prevent insulin from moving glucose into cells. Because the body does not use insulin properly, glucose rises to unsafe levels in the blood.

Over time, sustained hyperglycemia leads to glucotoxicity, which worsens insulin resistance and contributes to dysfunction in the beta cells of the pancreas. The degree of sustained hyperglycemia is directly related to diabetic microvascular complications and may also contribute to macrovascular complications. In this way, hyperglycemia perpetuates a cycle of deleterious effects that exacerbate type 2 diabetes control and complications.

It is now widely accepted that glycemic control makes a difference in type II diabetes patients. The goal of diabetes therapy today is to achieve and maintain as near normal glycemia as possible to prevent the long-term microvascular and macrovascular complications associated with elevated glucose in the blood. Oral therapeutic options for the treatment of type II diabetes mellitus include compounds known as: sulfonylureas, biguanides (metformin), thiazolidinediones, and alpha-glucosidase inhibitors. The active agents from each class are generally administered to patients alone. However, once monotherapy becomes inadequate, combination therapy is an attractive and rational course of action for treating hyperglycemia.

Recently, a new class of anti-diabetics was discovered known as sodium-glucose transporter-2 inhibitors (SGLT2). SGLT2 inhibitors prevent the reabsorption of glucose into blood by the kidney. The kidney, at first, allows glucose to pass from the blood into the bladder. Once in the urine, however, glucose is reabsorbed back into the blood via the renal proximal tubules. Ninety percent of glucose reuptake in the kidney occurs in via the renal proximal tubules. SGLT2 is a protein predominantly expressed in the renal proximal tubules and is likely to be the major transporter responsible for this reuptake.

Accordingly, the present invention provides pharmaceutical formulations that comprise metformin and an SGLT2 inhibitor, such as dapagliflozin, for oral administration in the treatment of diseases or disorders associated with SGLT2 activity. The metformin/SGLT2 formulations of the present invention provide an antidiabetic therapy to patients that is both convenient and effective for controlling blood glucose levels.

However, to successfully formulate a pharmaceutical composition comprising the combination of dapagliflozin or dapagliflozin (S) propylene glycol hydrate and metformin into granules or into a tablet formulation is challenging for several reasons.

Firstly, the large drug-to-drug ratio between metformin and the SGLT2 inhibitor makes content uniformity, with respect to dapagliflozin or dapagliflozin (S) propylene glycol hydrate in the final formulation, an important issue. It is necessary to have this relatively small amount of dapagliflozin or dapagliflozin (S) propylene glycol hydrate evenly distributed throughout the final granules or tablet formulation and thus avoid any variation in content.

In addition, the large difference in physical properties between dapagliflozin or dapagliflozin (S) propylene glycol hydrate and metformin, and especially the poor compaction properties of metformin, make it difficult to produce tablets having acceptable mechanical strength.

After several unsuccessful attempts, including dry granulation by roller compaction and traditional wet granulation, it has now been found that both of the above requirements can be met by spraying a solution or a suspension comprising dapagliflozin or dapagliflozin (S) propylene glycol hydrate and a binder onto the metformin particles in a fluid bed equipment, thereby producing granules that have uniform dapagliflozin or dapagliflozin (S) propylene glycol hydrate content and good compaction properties. The good compaction properties of these granules are thought to result from the way the granules are formed during the spray granulation process together with the fact that this process makes it possible to use larger amounts of a binder than was possible in the earlier tested granulation processes. The way in which the granules are built up during the spray granulation process gives them suitable density/porosity and a suitable particle size distribution with little variation between batches. The granules also have superior flow properties.

It has further been found that these beneficial formulations can be achieved while maintaining the chemical stability of the dapagliflozin or dapagliflozin (S) propylene glycol hydrate despite using a process in which at least part of the dapagliflozin is dissolved in water.

SUMMARY OF THE DISCLOSURE

In one aspect, the present invention provides an immediate release pharmaceutical formulation which includes a tablet, a stock granulation, or a capsule formulation comprising (1) an SGLT2 inhibitor or a pharmaceutically acceptable salt or solvate thereof, (2) metformin or a pharmaceutically acceptable salt or solvate thereof, and (3) optionally a coating. Metformin hydrochloride (HCl) is preferred. A preferred SGLT2 inhibitor is dapagliflozin, dapagliflozin (S) propylene glycol hydrate (1:1:1), or dapagliflozin (R) propylene glycol hydrate (1:1:1). The most preferred SGLT2 inhibitor is dapagliflozin or dapagliflozin (S) propylene glycol hydrate (1:1:1).

In another aspect, the present invention provides methods of treating diseases or disorders associated with SGLT2 activity comprising administering to a mammal in need of such treatment a therapeutically effective amount of a pharmaceutical formulation of the present invention. The pharmaceutical formulations of the present invention can be administered to mammals, preferably humans, for the treatment of a variety of conditions and disorders associated with SGLT2 activity including, but not limited to, treating or delaying the progression or onset of diabetes (including Type I and Type II diabetes), impaired glucose tolerance, insulin resistance, and diabetic complications, such as nephropathy, retinopathy, neuropathy and cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis, and hypertension. The formulations of the present invention can also be utilized to increase the blood levels of high density lipoprotein (HDL). In addition, the conditions, diseases, and maladies collectively referenced to as "Syndrome X" or Metabolic Syndrome, can be treated employing the formulations of the present invention.

In another aspect, the invention provides methods for preparing an immediate release pharmaceutical formulation which includes a tablet, a stock granulation, or a capsule formulation comprising metformin or a pharmaceutically acceptable salt or solvate thereof, and the sodium dependent glucose transporter (SGLT2) inhibitor or a pharmaceutically acceptable salt or solvate thereof.

DETAILED DESCRIPTION OF THE DISCLOSURE

Figure 1:
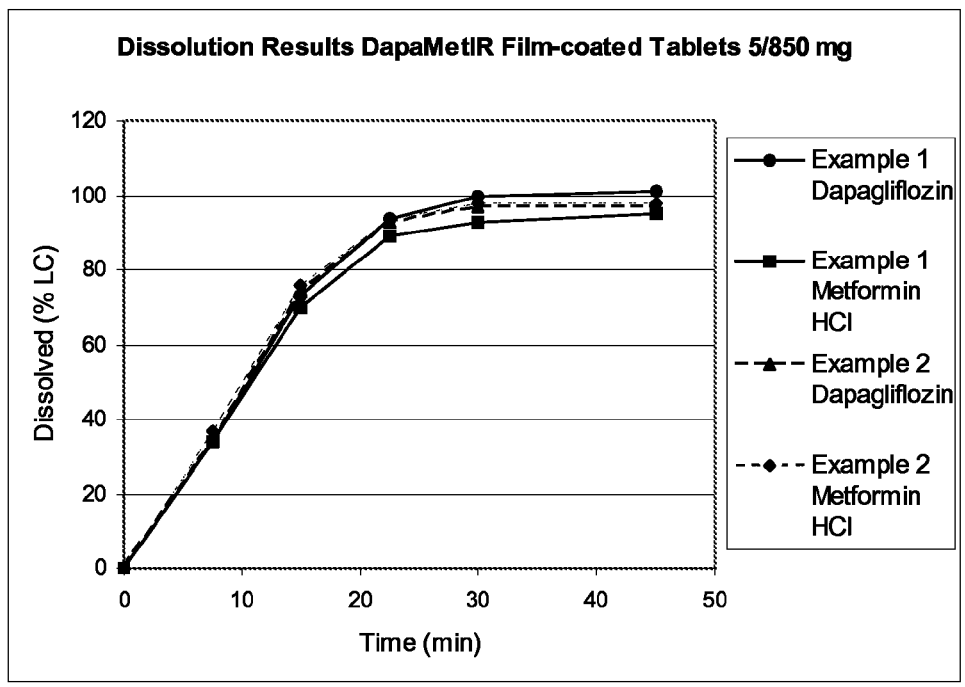
FIG. 1 describes a dissolution profile for the immediate release formulations (film-coated) of Examples 1 and 2 that comprise dapagliflozin and metformin.

The present invention provides immediate release formulations comprising dapagliflozin or dapagliflozin (S) propylene glycol hydrate and metformin in combination with other excipients. The formulations are in the form of a tablet, granulation, or capsule, where a tablet form is preferred. The formulations contain a combination of excipients and are manufactured using a method that provides content uniformity, desirable tensile strength and suitable disintegration and dissolution times in a tablet combining a low dose component with a high dose component. Preferred tablet properties include a tensile strength about 2 MPa (megapascal), a disintegration time of about 20 minutes and dissolution exceeding 80% after 30 minutes. The formulations of the present invention provide these desirable properties despite the large drug to drug ratio between metformin (500-1000 mgs) and the SGLT2 inhibitor (1.25-5.0 mgs) and despite the known problem of slow disintegration of tablets containing a high metformin content.

Accordingly, the present invention provides immediate release pharmaceutical formulations that comprise an SGLT2 inhibitor, metformin, one or more binders, one or more fillers, one or more disintegrants, one or more lubricants, and optionally a coating. The preferred SGLT2 inhibitor is dapagliflozin or dapagliflozin (S) propylene glycol hydrate (1:1:1). Preferred amounts of dapagliflozin are between 1 and 6 mgs or between 1.2 and 7.4 mgs for dapagliflozin (S) propylene glycol hydrate. The most preferred amounts of dapagliflozin are 2.5 mgs and 5.0 mgs and the most preferred amounts of dapagliflozin (S) propylene glycol hydrate are 3.08 mgs and 6.15 mgs. Metformin hydrochloride is the preferred form of metformin. Preferred amounts of metformin are 500 mgs, 850 mgs, and 1000 mgs. The preferred binder is hydroxypropyl cellulose. The preferred filler is microcrystalline cellulose and magnesium stearate is the preferred lubricant. Sodium starch glycolate or hydroxypropyl cellulose is the preferred disintegrant where the most preferred disintegrant is sodium starch glycolate. The formulations are in the form of a tablet, granulation, or capsule, where tablets are the preferred form. The optional coating is selected from Opadry® II white, Opadry® II brown, Opadry® II orange, or Opadry® II yellow.

The term content uniformity (CU) is defined as the variability in content between individual tablets derived from the same batch. CU is measured to ensure the consistency of dosage units, i e, that each unit in a batch should have an active substance content within a narrow range around the target strength such that the batch falls within the specification limits set. CU is reported as relative standard deviation in percent (% RSD).

The mechanical strength of the tablets is determined by a method called diametral compression testing. This consists of subjecting a disc specimen, e.g. a tablet, to two diametrically opposed point loads. The force is continuously increased until the tablet breaks. The crushing strength (N) is divided by the break area of the tablet ($mm^2$) in order to compensate for the size of the tablet. The result obtained is referred to herein as the tensile strength (TS) of the tablet and is measured in MPa.

In another aspect, the present invention provides immediate release pharmaceutical formulations that comprise about 0.1-2% dapagliflozin or dapagliflozin (S) propylene glycol hydrate; about 55-85% metformin hydrochloride; about 1-15% hydroxypropyl cellulose; about 2-25% microcrystalline cellulose; about 1-12% sodium starch glycolate or about 3-10% hydroxypropyl cellulose, low substituted; and about 0.25-5% magnesium stearate. The optional coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.1-1% dapagliflozin or dapagliflozin (S) propylene glycol hydrate; about 60-80% metformin hydrochloride; about 1-10% hydroxypropyl cellulose; about 2-25% microcrystalline cellulose; about 4-10% sodium starch glycolate or about 3-10% hydroxypropyl cellulose, low substituted; and about 0.25-2.5% magnesium stearate. The optional coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.25-0.8% dapagliflozin or dapagliflozin (S) propylene glycol hydrate; about 62-77% metformin hydrochloride; about 3-10% hydroxypropyl cellulose; about 5-21% microcrystalline cellulose; about 5-9% sodium starch glycolate or about 5-8% hydroxypropyl cellulose, low substituted; and about 0.6-1.4% magnesium stearate. The optional coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.5% dapagliflozin or dapagliflozin (S) propylene glycol hydrate; about 70.5% metformin hydrochloride; about 8% hydroxypropyl cellulose; about 12.5% microcrystalline cellulose; about 8% sodium starch glycolate; and about 0.6% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.25% dapagliflozin or dapagliflozin (S) propylene glycol hydrate; about 71% metformin hydrochloride; about 8% hydroxypropyl cellulose; about 12.5% microcrystalline cellulose; about 8% sodium starch glycolate; and about 0.6% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.4% dapagliflozin or dapagliflozin (S) propylene glycol hydrate; about 61.5% metformin hydrochloride; about 8% hydroxypropyl cellulose; about 21% microcrystalline cellulose; about 8.5% sodium starch glycolate; and about 1.4% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.4% dapagliflozin or dapagliflozin (S) propylene glycol hydrate; about 72% metformin hydrochloride; about 9% hydroxypropyl cellulose; about 12.5% microcrystalline cellulose; about 5% sodium starch glycolate; and about 1% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.5% dapagliflozin or dapagliflozin (S) propylene glycol hydrate; about 70.5% metformin hydrochloride; about 5.5% hydroxypropyl cellulose; about 20.5% microcrystalline cellulose; about 5% sodium starch glycolate; and about 1% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.5% dapagliflozin or dapagliflozin (S) propylene glycol hydrate; about 75.5% metformin hydrochloride; about 6% hydroxypropyl cellulose; about 12.5% microcrystalline cellulose; about 5% sodium starch glycolate; and about 0.6% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.5% dapagliflozin or dapagliflozin (S) propylene glycol hydrate; about 77% metformin hydrochloride; about 10% hydroxypropyl cellulose; about 5% microcrystalline cellulose; about 7.5% sodium starch glycolate; and about 0.6% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.8% dapagliflozin or dapagliflozin (S) propylene glycol hydrate; about 69% metformin hydrochloride; about 3% hydroxypropyl cellulose; about 20% microcrystalline cellulose; about 6.5% hydroxypropyl cellulose, low substituted; and about 0.8% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.4% dapagliflozin or dapagliflozin (S) propylene glycol hydrate; about 68% metformin hydrochloride; about 2.6% hydroxypropyl cellulose; about 20% microcrystalline cellulose; about 8% sodium starch glycolate; and about 0.6% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.2% dapagliflozin or dapagliflozin (S) propylene glycol hydrate; about 70.7% metformin hydrochloride; about 8% hydroxypropyl cellulose; about 12.5% microcrystalline cellulose; about 8% sodium starch glycolate; and about 0.6% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 2.5 mgs of dapagliflozin or about 3.08 mgs of dapagliflozin (S) propylene glycol hydrate; about 500 mgs of metformin hydrochloride; optionally one or more binders, optionally one or more fillers, optionally one or more disintegrants, optionally one or more lubricants, and optionally a coating.

In another aspect, the present invention provides immediate release pharmaceutical formulations that comprise about 2.5 mgs of dapagliflozin or about 3.08 mgs of dapagliflozin (S) propylene glycol hydrate; about 500 mgs of metformin hydrochloride; about 19 mgs hydroxypropyl cellulose; about 150 mgs microcrystalline cellulose; about 60 mgs sodium starch glycolate; and about 4.5 mgs magnesium stearate. The coating can be Opadry® II white, Opadry® II orange, Opadry® II brown, or Opadry® II yellow. The preferred coating can be Opadry® II white. The pharmaceutical formulation is in the form of a tablet, a stock granulation, or a capsule.

In another aspect, the present invention provides immediate release pharmaceutical formulations that comprise about 2.5 mgs of dapagliflozin or about 3.08 mgs of dapagliflozin (S) propylene glycol hydrate; about 850 mgs of metformin hydrochloride; optionally one or more binders, optionally one or more fillers, optionally one or more disintegrants, optionally one or more lubricants, and optionally a coating.

In another aspect, the present invention provides immediate release pharmaceutical formulations that comprise about 2.5 mgs of dapagliflozin or about 3.08 mgs of dapagliflozin (S) propylene glycol hydrate; about 850 mgs of metformin hydrochloride; about 96 mgs hydroxypropyl cellulose; about 150 mgs microcrystalline cellulose; about 96 mgs sodium starch glycolate; and about 7 mgs magnesium stearate. The coating can be Opadry® II white, Opadry®II orange, Opadry® II brown, or Opadry® II yellow. The preferred coating can be Opadry® II white. The pharmaceutical formulation is in the form of a tablet, a stock granulation, or a capsule.

In another aspect, the present invention provides immediate release pharmaceutical formulations that comprise about 5 mgs of dapagliflozin or about 6.15 mgs of dapagliflozin (S) propylene glycol hydrate; about 850 mgs of metformin hydrochloride; optionally one or more binders, optionally one or more fillers, optionally one or more disintegrants, optionally one or more lubricants, and optionally a coating.

In another aspect, the present invention provides immediate release pharmaceutical formulations that comprise about 5 mgs of dapagliflozin or about 6.15 mgs of dapagliflozin (S) propylene glycol hydrate; about 850 mgs of metformin hydrochloride; about 97 mgs hydroxypropyl cellulose; about 151 mgs microcrystalline cellulose; about 97 mgs sodium starch glycolate; and about 7 mgs magnesium stearate. The coating can be Opadry® II white, Opadry® II orange, Opadry® II brown, or Opadry® II yellow. The preferred coating can be Opadry® II brown. The pharmaceutical formulation is in the form of a tablet, a stock granulation, or a capsule.

In another aspect, the present invention provides immediate release pharmaceutical formulations that comprise about 2.5 mgs of dapagliflozin or about 3.08 mgs of dapagliflozin (S) propylene glycol hydrate; about 1000 mgs of metformin hydrochloride; optionally one or more binders, optionally one or more fillers, optionally one or more disintegrants, optionally one or more lubricants, and optionally a coating.

In another aspect, the present invention provides immediate release pharmaceutical formulations that comprise about 2.5 mgs of dapagliflozin or about 3.08 mgs of dapagliflozin (S) propylene glycol hydrate; about 1000 mgs of metformin hydrochloride; about 113 mgs hydroxypropyl cellulose; about 177 mgs microcrystalline cellulose; about 113 mgs sodium starch glycolate; and about 9 mgs magnesium stearate. The coating can be Opadry® II white, Opadry®II orange, Opadry® II brown, or Opadry® II yellow. The preferred coating can be Opadry® II orange. The pharmaceutical formulation is in the form of a tablet, a stock granulation, or a capsule.

In another aspect, the present invention provides immediate release pharmaceutical formulations that comprise about 5 mgs of dapagliflozin or about 6.15 mgs of dapagliflozin (S) propylene glycol hydrate; about 1000 mgs of metformin hydrochloride; optionally one or more binders, optionally one or more fillers, optionally one or more disintegrants, optionally one or more lubricants, and optionally a coating.

In another aspect, the present invention provides immediate release pharmaceutical formulations that comprise about 5 mgs of dapagliflozin or about 6.15 mgs of dapagliflozin (S) propylene glycol hydrate; about 1000 mgs of metformin hydrochloride; about 114 mgs hydroxypropyl cellulose; about 177 mgs microcrystalline cellulose; about 114 mgs sodium starch glycolate; and about 9 mgs magnesium stearate. The coating can be Opadry® II white, Opadry® II orange, Opadry® II brown, or Opadry® II yellow. The preferred coating can be Opadry® II yellow. The pharmaceutical formulation is in the form of a tablet, a stock granulation, or a capsule.

The present invention also provides methods of treating a disorder or disease associated with SGLT2 activity that includes diabetes (including type I and type II diabetes), impaired glucose tolerance, insulin resistance, nephropathy, retinopathy, neuropathy and cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis or hypertension in a mammal comprising administering to the mammal in need of such treatment a pharmaceutical formulation that comprises: (1) an SGLT2 inhibitor; (2) metformin; and (3) optionally a coating; wherein the pharmaceutical formulation is immediate release and in the form of a tablet, a stock granulation, or a capsule. The preferred method treats type II diabetes in a human. The preferred SGLT2 inhibitor is dapagliflozin or dapagliflozin (S) propylene glycol hydrate.

In another aspect, the present invention provides a method to treat type II diabetes in a human comprising administering to the human in need of such treatment a pharmaceutical formulation that comprises an SGLT2 inhibitor; metformin; one or more binders; one or more fillers; one or more disintegrants; and one or more lubricants. The preferred SGLT2 inhibitor is dapagliflozin or dapagliflozin (S) propylene glycol hydrate. The pharmaceutical formulation is an immediate release formulation in the form of a tablet, granulation, or capsule.

In another aspect, the present invention provides a method to treat type II diabetes in a human comprising administering to the human in need of such treatment a pharmaceutical formulation that comprises dapagliflozin or dapagliflozin (S) propylene glycol hydrate; metformin hydrochloride; hydroxypropyl cellulose; microcrystalline cellulose; disintegrant is sodium starch glycolate or hydroxypropyl cellulose, low substituted; and the lubricant is magnesium stearate. The pharmaceutical formulation is an immediate release formulation in the form of a tablet, granulation, or capsule.

In another aspect, the present invention provides a method to treat type II diabetes in a human comprising administering to the human in need of such treatment a pharmaceutical formulation that comprises about 0.1-2% dapagliflozin or dapagliflozin (S) propylene glycol hydrate; about 55-85% metformin hydrochloride; about 1-15% hydroxypropyl cellulose; about 2-25% microcrystalline cellulose; about 1-12% sodium starch glycolate or 3-10% hydroxypropyl cellulose, low substituted; and about 0.25-5% magnesium stearate. The pharmaceutical formulation is an immediate release formulation in the form of a tablet, granulation, or capsule.

In another aspect, the present invention provides a method to treat type II diabetes in a human comprising administering to the human in need of such treatment a pharmaceutical formulation that comprises about 0.1-1% dapagliflozin or dapagliflozin (S) propylene glycol hydrate; about 60-80% metformin hydrochloride; about 1-10% hydroxypropyl cellulose; about 2-25% microcrystalline cellulose; about 4-10% sodium starch glycolate or about 3-10% hydroxypropyl cellulose, low substituted; and about 0.25-2.5% magnesium stearate. The optional coating can be Opadry® II white, Opadry® II orange, Opadry® II brown, or Opadry® II yellow. The pharmaceutical formulation is in the form of a tablet, a stock granulation, or a capsule.

In another aspect, the present invention provides a method to treat type II diabetes in a human comprising administering to the human in need of such treatment a pharmaceutical formulation that comprises about 0.25-0.8% dapagliflozin or dapagliflozin (S) propylene glycol hydrate; about 62-77% metformin hydrochloride; about 3-10% hydroxypropyl cellulose; about 5-21% microcrystalline cellulose; about 5-9% sodium starch glycolate or 5-8% hydroxypropyl cellulose, low substituted; and about 0.6-1.4% magnesium stearate. The pharmaceutical formulation is an immediate release formulation in the form of a tablet, granulation, or capsule.

In another aspect, the present invention provides a method to treat type II diabetes in a human comprising administering to the human in need of such treatment a pharmaceutical formulation that comprises about 0.5% dapagliflozin or dapagliflozin (S) propylene glycol hydrate; about 70.5% metformin hydrochloride; about 8% hydroxypropyl cellulose; about 12.5% microcrystalline cellulose; about 8% sodium starch glycolate; and about 0.6% magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 0.25% dapagliflozin or dapagliflozin (S) propylene glycol hydrate; about 71% metformin hydrochloride; about 8% hydroxypropyl cellulose; about 12.5% microcrystalline cellulose; about 8% sodium starch glycolate; and about 0.6% magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 0.4% dapagliflozin or dapagliflozin (S) propylene glycol hydrate; about 61.5% metformin hydrochloride; about 8% hydroxypropyl cellulose; about 21% microcrystalline cellulose; about 8.5% sodium starch glycolate; and about 1.4% magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 0.4% dapagliflozin or dapagliflozin (S) propylene glycol hydrate; about 72% metformin hydrochloride; about 9% hydroxypropyl cellulose; about 12.5% microcrystalline cellulose; about 5% sodium starch glycolate; and about 1% magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 0.5% dapagliflozin or dapagliflozin (S) propylene glycol hydrate; about 70.5% metformin hydrochloride; about 5.5% hydroxypropyl cellulose; about 20.5% microcrystalline cellulose; about 5% sodium starch glycolate; and about 1% magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 0.5% dapagliflozin or dapagliflozin (S) propylene glycol hydrate; about 75.5% metformin hydrochloride; about 6% hydroxypropyl cellulose; about 12.5% microcrystalline cellulose; about 5% sodium starch glycolate; and about 0.6% magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 0.5% dapagliflozin or dapagliflozin (S) propylene glycol hydrate; about 77% metformin hydrochloride; about 10% hydroxypropyl cellulose; about 5% microcrystalline cellulose; about 7.5% sodium starch glycolate; and about 0.6% magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 0.8% dapagliflozin or dapagliflozin (S) propylene glycol hydrate; about 69% metformin hydrochloride; about 3% hydroxypropyl cellulose; about 20% microcrystalline cellulose; about 6.5% hydroxypropyl cellulose, low substituted; and about 0.8% magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides immediate release pharmaceutical formulations that comprise about 0.4% dapagliflozin or dapagliflozin (S) propylene glycol hydrate; about 68% metformin hydrochloride; about 2.6% hydroxypropyl cellulose; about 20% microcrystalline cellulose; about 8% sodium starch glycolate; and about 0.6% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides immediate release pharmaceutical formulations that comprise about 0.2% dapagliflozin or dapagliflozin (S) propylene glycol hydrate; about 70.7% metformin hydrochloride; about 8% hydroxypropyl cellulose; about 12.5% microcrystalline cellulose; about 8% sodium starch glycolate; and about 0.6% magnesium stearate. The coating can be Opadry® II white, Opadry® II orange, Opadry® II brown, or Opadry® II yellow. The pharmaceutical formulation is in the form of a tablet, a stock granulation, or a capsule.

In another aspect, the present invention provides a method to treat type II diabetes in a human comprising administering to the human in need of such treatment a pharmaceutical formulation that comprises about 2.5 mgs of dapagliflozin or about 3.08 mgs of dapagliflozin (S) propylene glycol hydrate; about 500 mgs of metformin hydrochloride; about 19 mgs hydroxypropyl cellulose; about 150 mgs microcrystalline cellulose; about 60 mgs sodium starch glycolate; and about 4.5 mgs magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 2.5 mgs of dapagliflozin or about 3.08 mgs of dapagliflozin (S) propylene glycol hydrate, about 850 mgs of metformin hydrochloride; about 96 mgs hydroxypropyl cellulose; about 150 mgs microcrystalline cellulose; about 96 mgs sodium starch glycolate; and about 7 mgs magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 5 mgs of dapagliflozin or about 6.15 mgs of dapagliflozin (S) propylene glycol hydrate; about 850 mgs of metformin hydrochloride; about 97 mgs hydroxypropyl cellulose; about 151 mgs microcrystalline cellulose; about 97 mgs sodium starch glycolate; and about 7 mgs magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 2.5 mgs of dapagliflozin or about 3.08 mgs of dapagliflozin (S) propylene glycol hydrate; about 1000 mgs of metformin hydrochloride; about 113 mgs hydroxypropyl cellulose; about 177 mgs microcrystalline cellulose; about 113 mgs sodium starch glycolate; about 9 mgs magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

In another aspect, the present invention provides a method to treat type II diabetes in a human comprising administering to the human in need of such treatment a pharmaceutical formulation that comprises about 5 mgs of dapagliflozin or about 6.15 mgs of dapagliflozin (S) propylene glycol hydrate; about 1000 mgs of metformin hydrochloride; about 114 mgs hydroxypropyl cellulose; about 177 mgs microcrystalline cellulose; about 114 mgs sodium starch glycolate; about 9 mgs magnesium stearate. The pharmaceutical formulation is an immediate release formulation in the form of a tablet, granulation, or capsule, where tablet is preferred. The coating can be Opadry® II white, Opadry® II brown, Opadry® II orange, or Opadry® II yellow.

To prepare the formulations of the present invention, methods were developed to achieve acceptable chemical stability and content uniformity of dapagliflozin and/or dapagliflozin propylene glycol hydrate and to obtain acceptable tablet tensile strength, and desired dissolution and disintegration rates. A more in depth discussion with regard to mechanical strength of tablets and uniformity of content can be found in "Pharmaceutics: The Science of Dosage Form Design," Second Edition, Ed. M. E. Aulton (2002) (Church Livingstone), pages 417-423, the disclosure of which is herein incorporated by reference for any purpose.

Figure 3:
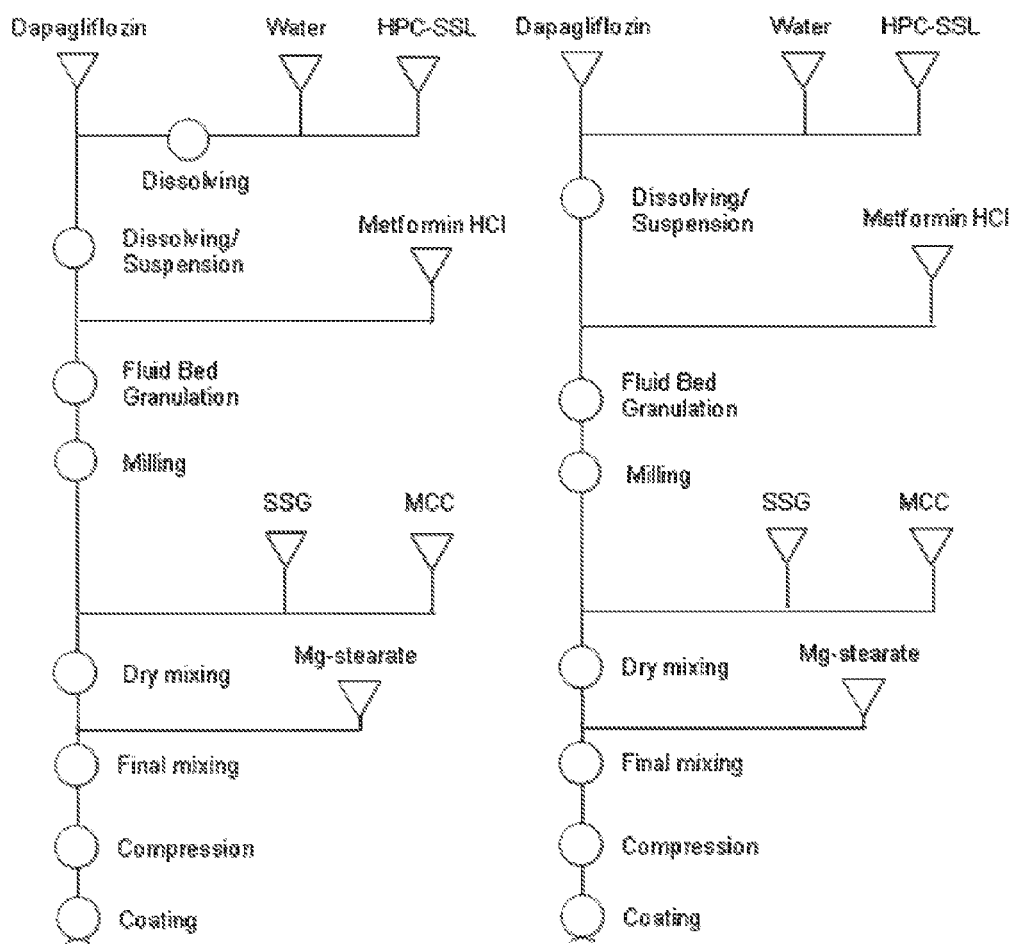
FIG. 3 describes methods of preparing formulations of the present invention in a flow chart.

Accordingly, the present invention provides methods of preparing an immediate release formulation that comprises: (1) an SGLT2 inhibitor or a pharmaceutically acceptable salt or solvate thereof, (2) metformin or a pharmaceutically acceptable salt or solvate thereof, and (3) optionally a coating. Preferred methods of preparing the formulations of the present invention are described in FIG. 3. One method comprises: (a) dissolving a binder in water to obtain a binder-solution; (b) adding an SGLT2 inhibitor to the binder-solution to obtain an SGLT2 inhibitor-binder-water solution or a suspension of SGLT2 inhibitor-binder-water; (c) spraying the SGLT2 inhibitor-binder-water solution or suspension on metformin in a fluidised bed, thereby performing a fluid bed granulation to obtain granules; (d) milling the granules; (e) mixing the granules with a filler and a disintegrant; (f) further mixing with a lubricant to obtain a final mixture; (g) compressing the final mixture into tablets; and (h) optionally coating the tablets. An alternative method comprises: (a) simultaneously adding a binder and an SGLT2 inhibitor to water; (b) dissolving the binder and part or all of the SGLT2 inhibitor to obtain a SGLT2 inhibitor-binder-water solution or a suspension of the SGLT2 inhibitor-binder-water; (c) spraying the SGLT2 inhibitor-binder-water solution or suspension on metformin in a fluidised bed, thereby performing a fluid bed granulation to obtain granules; (d) milling the granules; (e) mixing the granules with a filler and a disintegrant; (f) further mixing with a lubricant to obtain a final mixture; (g) compressing the final mixture into tablets; and (h) optionally coating the tablets.

Formulations comprising dapagliflozin or dapagliflozin (S) propylene glycol hydrate are the preferred formulations prepared by this process. In a preferred embodiment, this method prepares formulations that comprise 0.25-0.8% dapagliflozin or dapagliflozin (S)-propylene glycol hydrate; about 62-77% metformin hydrochloride; about 3-10% hydroxypropyl cellulose; about 5-21% microcrystalline cellulose; about 5-9% sodium starch glycolate; and about 0.6-1.4% magnesium stearate. In a more preferred embodiment, this method prepares formulations that comprise about 0.1-1% dapagliflozin or dapagliflozin (S) propylene glycol hydrate; about 60-80% metformin hydrochloride; about 1-10% hydroxypropyl cellulose; about 2-25% microcrystalline cellulose; about 4-10% sodium starch glycolate or about 3-10% hydroxypropyl cellulose, low substituted; and about 0.25-2.5% magnesium stearate. The formulations prepared by the methods described herein have good content uniformity with respect to dapagliflozin or dapagliflozin (S)-propylene glycol hydrate, tensile strength about 2 MPa (megapascal), disintegration time of 20 minutes, dissolution exceeding 80% after 30 minutes, and the lowest tablet weight possible, given the tablet strength.

In another aspect, the present invention provides methods of preparing an immediate release formulation that comprises: (1) an SGLT2 inhibitor or a pharmaceutically acceptable salt or solvate thereof, (2) metformin or a pharmaceutically acceptable salt or solvate thereof, and (3) optionally a coating. One method comprises: (a) dissolving hydroxypropyl cellulose SSL in water to obtain a HPC-solution; (b) adding an SGLT2 inhibitor to the HPC-solution to obtain an SGLT2 inhibitor-HPC-water solution or a suspension of SGLT2 inhibitor-HPC-water; (c) spraying the SGLT2 inhibitor-HPC-water solution or suspension on metformin in a fluidised bed, thereby performing a fluid bed granulation to obtain granules; (d) milling the granules; (e) mixing the granules with microcrystalline cellulose and sodium starch glycolate; (f) further mixing with magnesium stearate to obtain a final mixture; (g) compressing the final mixture into tablets and (h) optionally coating the tablets.

An alternative method comprises: (a) simultaneously adding hydroxypropyl cellulose SSL and an SGLT2 inhibitor to water; (b) dissolving the hydroxypropyl cellulose SSL and part or all of the SGLT2 inhibitor to obtain a SGLT2 inhibitor-HPC-water solution or a suspension of the SGLT2 inhibitor-HPC-water; (c) spraying the SGLT2 inhibitor-HPC-water solution or suspension on metformin in a fluidised bed, thereby performing a fluid bed granulation to obtain granules; (d) milling the granules; (e) mixing the granules with a filler and a disintegrant; (f) further mixing with a lubricant to obtain a final mixture; (g) compressing the final mixture into tablets; and (h) optionally coating the tablets.

In another aspect, the present invention provides methods of preparing an immediate release formulation that comprises: (1) dapagliflozin or a pharmaceutically acceptable salt or solvate thereof, (2) metformin or a pharmaceutically acceptable salt or solvate thereof, and (3) optionally a coating. One method comprises: (a) dissolving hydroxypropyl cellulose SSL in water to obtain a HPC-solution; (b) adding dapagliflozin or dapagliflozin (S) propylene glycol hydrate to the HPC-solution to obtain a dapagliflozin-HPC SSL-water solution or a suspension of dapagliflozin-HPC SSL-water; (c) spraying the dapagliflozin-HPC SSL-water suspension on metformin in fluidised bed, thereby performing a fluid bed granulation to obtain granules; (d) milling the granules; (e) mixing the granules with microcrystalline cellulose and sodium starch glycolate; (f) further mixing with magnesium stearate to obtain a final mixture; (g) compressing the final mixture into tablets and (h) optionally coating the tablets.

An alternative method comprises: (a) simultaneously adding hydroxypropyl cellulose SSL and dapagliflozin or dapagliflozin (S) propylene glycol hydrate to water; (b) dissolving the hydroxypropyl cellulose SSL and part or all of the dapagliflozin or dapagliflozin (S) propylene glycol hydrate to obtain a dapagliflozin-HPC-water solution or a suspension of dapagliflozin-HPC-water; (c) spraying the dapagliflozin-HPC-water solution or suspension on metformin in a fluidised bed, thereby performing a fluid bed granulation to obtain granules; (d) milling the granules; (e) mixing the granules with a filler and a disintegrant; (f) further mixing with a lubricant to obtain a final mixture; (g) compressing the final mixture into tablets; and (h) optionally coating the tablets.

In one embodiment, the formulation prepared by this method is about 0.25-0.8% dapagliflozin or dapagliflozin (S)-propylene glycol hydrate; about 62-77% metformin hydrochloride; about 3-10% hydroxypropyl cellulose; about 5-21% microcrystalline cellulose; about 5-9% sodium starch glycolate; and about 0.6-1.4% magnesium stearate. In a more preferred embodiment, this method prepares formulations that comprise about 0.1-1% dapagliflozin or dapagliflozin (S) propylene glycol hydrate; about 60-80% metformin hydrochloride; about 1-10% hydroxypropyl cellulose; about 2-25% microcrystalline cellulose; about 4-10% sodium starch glycolate or about 3-10% hydroxypropyl cellulose, low substituted; and about 0.25-2.5% magnesium stearate.

In a preferred embodiment the SGLT2 inhibitor and the binder are mixed at a temperature in the range of 5 to 65° C. In a more preferred embodiment the SGLT2 inhibitor and the binder are mixed at a temperature in the range of 40 to 60° C. In a most preferred embodiment the SGLT2 inhibitor and the binder are mixed at a temperature in the range of 45 to 55° C.

The formulations prepared by the methods described herein have good content uniformity with respect to dapagliflozin or dapagliflozin (S)-propylene glycol hydrate, tensile strength about 2 MPa (megapascal), disintegration time of 20 minutes, dissolution exceeding 80% after 30 minutes, and the lowest tablet weight possible, given the tablet strength.

Examples of bulking agents or fillers or compression agents suitable for use herein include, but are not limited to, cellulose derivatives, such as microcrystalline cellulose or wood cellulose (including microcrystalline cellulose 302), lactose, lactose anhydrous, sucrose, starch, pregelatinized starch, dextrose, mannitol (including mannitol Pearlitol SD 200), fructose, xylitol, sorbitol, corn starch, modified corn starch, inorganic salts such as calcium carbonate, calcium phosphate, dicalcium phosphate, calcium sulfate, dextrin/dextrates, maltodextrin, compressible sugars, and other known bulking agents or fillers, and/or mixtures of two or more thereof. Several types of microcrystalline cellulose are suitable for use in the formulations described herein, for example, microcrystalline cellulose selected from the group consisting of Avicel® types: PH101, PH102, PH103, PH105, PH 112, PH113, PH200, PH301, and other types of microcrystalline cellulose, such as silicified microcrystalline cellulose. Several types of lactose are suitable for use in the formulations described herein, for example, lactose selected from the group consisting of anhydrous lactose, lactose monohydrate, lactose fast flow, directly compressible anhydrous lactose, and modified lactose monohydrate. The preferred filler or compression aid of the present invention is microcrystalline cellulose PH102.

Examples of binders suitable for use herein include, but are not limited to, methyl cellulose, carboxymethyl cellulose (including sodium carboxymethyl cellulose), hydroxypropyl cellulose (including HPC-SSL, HPC-SL, HPC-L, HPC-EXF, HPC-ELF, etc.), hydroxypropylmethyl cellulose, corn starch, pregelatinized starch, modified corn starch, polyvinyl pyrrolidone (PVP), hydroxypropyl methylcellulose (HPMC) (including hydroxypropyl methylcellulose 2208), lactose, gum acacia, gum arabic, gelatin, agar, ethyl cellulose, cellulose acetate, tragacanth, sodium alginate, pullulan, as well as a wax binder such as carnauba wax, paraffin, spermaceti, polyethylenes or microcrystalline wax, as well as other conventional binding agents and/or mixtures of two or more thereof. Preferred binders of the present invention are hydroxypropyl cellulose SSL, hydroxypropyl cellulose SL, hydroxypropyl cellulose ELF, polyvinyl alcohol-polyethylene glycol, and polyvinyl pyrrolidone. The most preferred binder is hydroxypropyl cellulose SSL.

Suitable HPC polymers for use as a binder in the present invention include those that have a molar mass distribution falling in the range of between 1000 and 400,000 g/mole, preferably between 1000 and 300,000 g/mole and more preferably between 1000 and 200,000 g/mole. Furthermore, suitable HPC polymers for use as a binder in the present invention, having a molar mass distribution as previously described, preferably have a weight average molar mass of less than 90,000 g/mole, more preferably of less than 70,000 g/mole and even more preferably of less than 40,000 g/mole. Additionally, suitable HPC polymers for use as a binder in the present invention, having a molar mass distribution as previously described, preferably have a number average molar mass of less than 50,000 g/mole, more preferably of less than 45,000 g/mole and even more preferably of less than 25,000 g/mole.

The weight average molar mass, $M_w$, is defined as $$M_w = \frac{\sum_i N_i M_i^2}{\sum_i N_i M_i},$$

where $N_i$ is the number of molecules of molar mass $M_i$.

The number average molar mass, $M_n$, is defined as $$M_n = \frac{\sum_i N_i M_i}{\sum_i N_i},$$

where N is the number of molecules of molar mass $M_i$.

Examples of disintegrants suitable for use herein include, but are not limited to, croscarmellose sodium, crospovidone, starch, potato starch, pregelatinized starch, corn starch, sodium starch glycolate, microcrystalline cellulose, low substituted hydroxypropyl cellulose LH21, polyvinyl pyrrolidone cross linked, and other known disintegrants. Several specific types of disintegrant are suitable for use in the formulations described herein. For example, any grade of crospovidone can be used, including for example crospovidone XL-10, and includes members selected from the group consisting of Kollidon CL®, Polyplasdone XL®, Kollidon Polyplasdone XL-10®, and Polyplasdone INF-10®. In one embodiment, the disintegrant, if present, of the stock granulation is sodium starch glycolate, croscarmellose sodium and/or crospovidone. The preferred disintegrants are sodium starch glycolate and low substituted hydroxypropyl cellulose LH21. The most preferred disintegrant is sodium starch glycolate.

Examples of lubricants suitable for use herein include, but are not limited to, magnesium stearate, zinc stearate, calcium stearate, talc, carnauba wax, stearic acid, palmitic acid, sodium stearyl fumarate sodium laurel sulfate, glyceryl palmitostearate, palmitic acid, myristic acid and hydrogenated vegetable oils and fats, as well as other known lubricants, and/or mixtures of two or more thereof. The preferred lubricant of the present invention is magnesium stearate.

Examples of glidants and/or anti-adherents suitable for use herein include but are not limited to, silicon dioxide, colloidal silicon dioxide, magnesium silicate, magnesium trisilicate, talc, and other forms of silicon dioxide, such as aggregated silicates and hydrated silica.

The coating of the tablet or capsule, where present, can include from about 10% to about 95% of polymer based on the weight of the coating layer, and can be prepared employing conventional procedures. The film coating of the tablet or capsule includes from about 20% to about 90% of polymer based on the weight of the coating layer. The formulation can contain at least one coating layer polymer and a coating solvent, for example, water, which is used for processing and removed by drying. Suitable examples of polymer for the coating layer include, but are not limited to, hydroxypropyl methylcellulose, polyvinyl alcohol (PVA), ethyl cellulose, methacrylic polymers, hydroxypropyl cellulose, and starch. The coating layer polymer can be PVA. The coating layer polymer can be hydroxypropyl cellulose. Use of PVA allows for enhanced logo definition, film adhesion, and facilitates faster coating of the drug, the latter of which can be important for dapagliflozin formulations due to the temperature sensitivity of the compound. The coating can also optionally include a plasticizer of from about 0% to about 30% by weight, based on the weight of the coating layer; e.g., the plasticizer is from about 15% to about 25% by weight of the coating layer. Suitable plasticizers include, but are not limited to, triacetin, diethyl phthalate, tributyl sebacate, polyethylene glycol (PEG), glycerin, triacetin, and triethyl citrate, for example. The plasticizer is polyethylene glycol of molecular weight 200 to 20,000, of molecular weight 400 to 4,000, or of molecular weight 400.

The coating can also optionally include an anti-adherent or glidant such as talc, fumed silica, or magnesium stearate, or an opacifying agent, such as titanium dioxide. The coating layer may optionally include one or more colorants, for example, iron oxide based colorant(s). Examples of commercially available coating material include Opadry® HP, Opadry® II white, Opadry® II yellow, Opadry® II orange, and Opadry® II brown. Opadry® II white 85F18422 comprises of polyvinyl alcohol, polyethylene glycol, titanium dioxide, and talc. Opadry® II PVA also includes Opadry® II Yellow 85F92582 comprised of polyvinyl alcohol, polyethylene glycol, titanium dioxide, talc, and yellow iron dioxide. Preferred coatings of the present invention are Opadry® II white, Opadry® II brown, Opadry® II orange, and Opadry® II yellow.

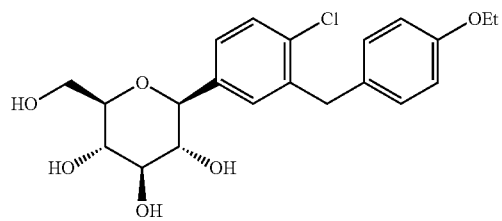 [SMILES: CCOc1ccc(Cc2cc([C@@H]3O[C@H](CO)[C@@H](O)[C@H](O)[C@H]3O)ccc2Cl)cc1]

Dapagliflozin-(2S,3R,4R,5S,6R)-2-(4-chloro-3-(4-ethoxybenzyl)phenyl)-6-(hydroxymethyl)tetrahydro-2H-pyran-3,4,5-triol (dapaglifozin)

Dapagliflozin can be prepared using similar procedures as described in U.S. Pat. No. 6,515,117 or international published applications no. WO 03/099836 and WO 2008/116179, the disclosures of which are herein incorporated by reference in their entirety for any purpose. SGLT2 $EC_{50}$=1.1 nM.

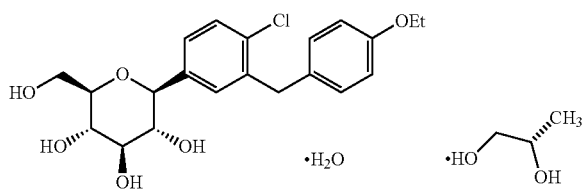

Dapgliflozin (S) PGS-(2S,3R,4R,5S,6R)-2-(4-chloro-3-(4-ethoxybenzyl)phenyl)-6-(hydroxymethyl)tetrahydro-2H-pyran-3,4,5-triol (S)-propane-1, 2-diol hydrate (1:1:1)

Dapagliflozin (S) propylene glycol hydrate (1:1:1) can be prepared using similar procedures as described in published applications WO 08/002,824 and WO 2008/116179, the disclosures of which are herein incorporated by reference in their entirety for any purpose. SGLT2 $EC_{50}$=1.1 nM.

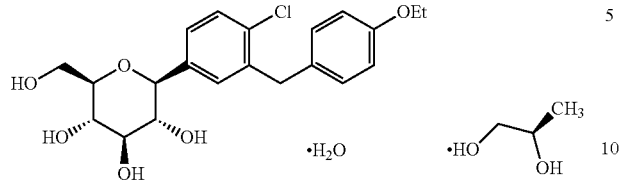

Dapagliflozin (R) PGS-(2S,3R,4R,5S,6R)-2-(4-chloro-3-(4-ethoxybenzyl)phenyl)-6-(hydroxymethyl)tetrahydro-2H-pyran-3,4,5-triol (R)-propane-1, 2-diol hydrate (1:1:1)

Dapagliflozin (R) propylene glycol hydrate (1:1:1) can be prepared using similar procedures as described in WO 08/002,824 and WO 2008/116179. The disclosures of which are herein incorporated by reference in their entirety for any purpose. SGLT2 $EC_{50}$=1.1 nM.

Different forms of the antidiabetic agent metformin are suitable for use in the formulations of the present invention's bilayer tablets including pharmaceutically acceptable salts thereof such as the hydrochloride, hydrobromide, fumarate, succinate, p-chlorophenoxy acetate or embonate. The fumarate and succinate salts are preferably metformin (2:1) fumarate, and metformin (2:1) succinate. Metformin hydrochloride is preferred.

The present invention also contemplates formulations wherein the SGLT2 inhibitor is a compound of Formula (I) as described in U.S. Pat. No. 6,414,126, herein incorporated by reference in its entirety for any purpose. Other SGLT2 inhibitors contemplated by the present invention include sergliflozin, remogliflozin, remogliflozin etabonate, canagliflozin, BI-10773 and BI-44847, ASP-1941, R-7201, LX-4211, YM-543, AVE 2268, TS-033 or SGL-0100, and the compounds disclosed in U.S. Pat. No. 7,589,193, WO2007007628, EP2009010, WO200903596, US2009030198, U.S. Pat. No. 7,288,528 and US 2007/0197623, herein incorporated by reference in their entirety for any purpose. The following SGLT2 inhibitors, in addition to dapagliflozin, are preferred:

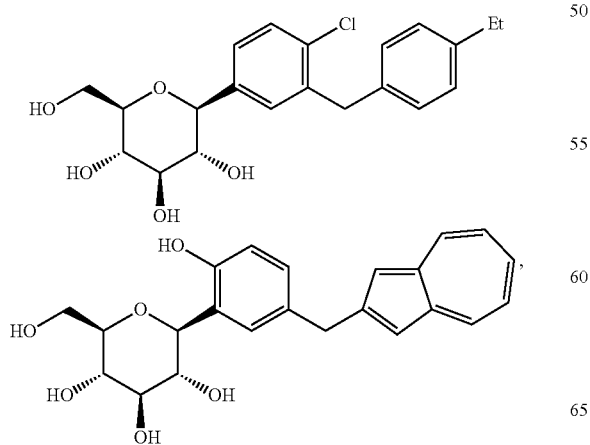

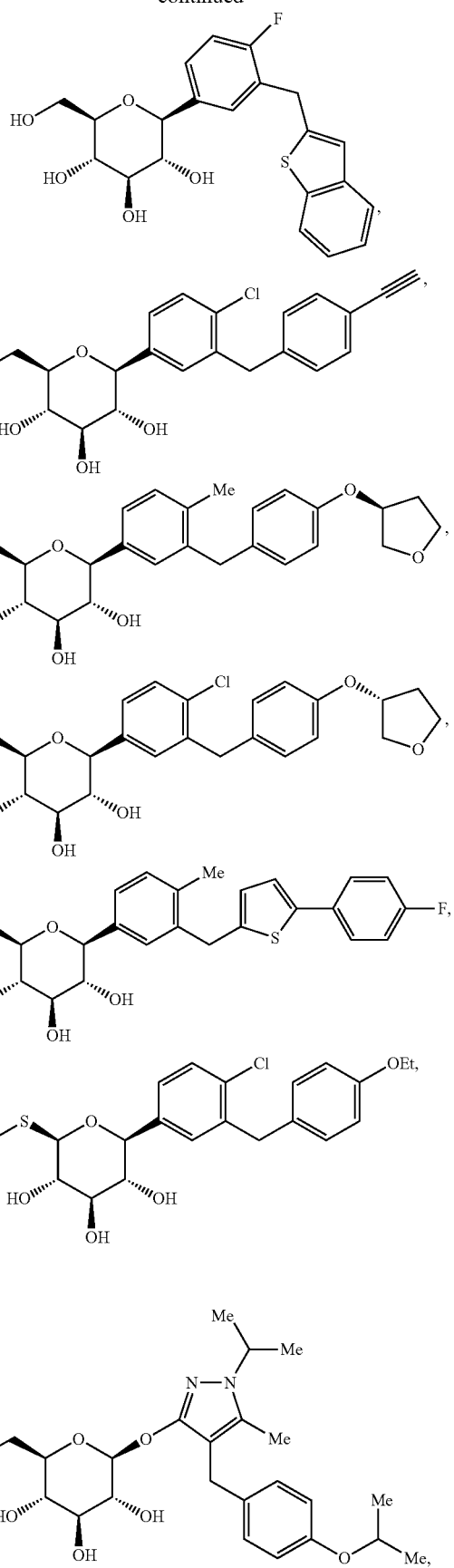

-continued

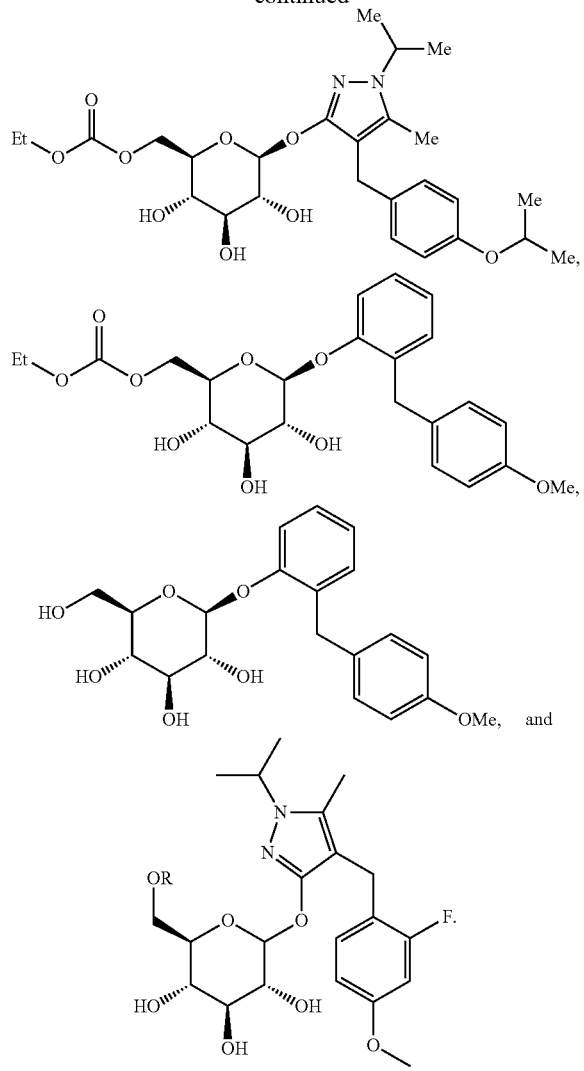

In another aspect, the present invention provides a use of a pharmaceutical formulation comprising metformin and a SGLT2 inhibitor for preparing, or for the manufacture of, a medicament for treating diabetes (including type I and type II diabetes), impaired glucose tolerance, insulin resistance, and diabetic complications, such as nephropathy, retinopathy, neuropathy and cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension.

In another aspect, the present invention provides a use of a pharmaceutical formulation comprising metformin; an SGLT2 inhibitor; one or more binders; one or more fillers; one or more disintegrants; one or more lubricants; and optionally a coating; for preparing, or for the manufacture of, a medicament for treating diabetes (including type I and type II diabetes), impaired glucose tolerance, insulin resistance, and diabetic complications, such as nephropathy, retinopathy, neuropathy and cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension.

In another aspect, the present invention provides a use of a pharmaceutical formulation comprising metformin; an SGLT2 inhibitor; hydroxypropyl cellulose; microcrystalline cellulose; sodium starch glycolate or hydroxypropyl cellulose, low substituted; magnesium stearate; and optionally a coating; for preparing, or for the manufacture of, a medicament for treating diabetes (including type I and type II diabetes), impaired glucose tolerance, insulin resistance, and diabetic complications, such as nephropathy, retinopathy, neuropathy and cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension.

In another aspect, the present invention provides a use of a pharmaceutical formulation comprising 0.25-0.8% dapagliflozin or dapagliflozin (S) propylene glycol hydrate; about 62-77% metformin hydrochloride; about 3-10% hydroxypropyl cellulose; about 5-21% microcrystalline cellulose; about 5-9% sodium starch glycolate or about 5-8% hydroxypropyl cellulose, low substituted; about 0.6-1.4% magnesium stearate; and optionally a coating; for preparing, or for the manufacture of, a medicament for treating diabetes (including type I and type II diabetes), impaired glucose tolerance, insulin resistance, and diabetic complications, such as nephropathy, retinopathy, neuropathy and cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension.

In another aspect, the present invention provides a use of a pharmaceutical formulation comprising about 0.5% dapagliflozin or dapagliflozin (S) propylene glycol hydrate; about 70.5% metformin hydrochloride; about 8% hydroxypropyl cellulose; about 12.5% microcrystalline cellulose; about 8% sodium starch glycolate; and about 0.6% magnesium stearate; for preparing, or for the manufacture of, a medicament for treating type II diabetes.

In another aspect, the present invention provides a use of a pharmaceutical formulation comprising about 0.25% dapagliflozin or dapagliflozin (S) propylene glycol hydrate; about 71% metformin hydrochloride; about 8% hydroxypropyl cellulose; about 12.5% microcrystalline cellulose; about 8% sodium starch glycolate; and about 0.6% magnesium stearate; for preparing, or for the manufacture of, a medicament for treating type II diabetes.

In another aspect, the present invention provides a use of a pharmaceutical formulation comprising about 0.4% dapagliflozin or dapagliflozin (S) propylene glycol hydrate; about 61.5% metformin hydrochloride; about 8% hydroxypropyl cellulose; about 21% microcrystalline cellulose; about 8.5% sodium starch glycolate; and about 1.4% magnesium stearate; for preparing, or for the manufacture of, a medicament for treating type II diabetes.

In another aspect, the present invention provides a use of a pharmaceutical formulation comprising about 0.4% dapagliflozin or dapagliflozin (S) propylene glycol hydrate; about 72% metformin hydrochloride; about 9% hydroxypropyl cellulose; about 12.5% microcrystalline cellulose; about 5% sodium starch glycolate; and about 1% magnesium stearate; for preparing, or for the manufacture of, a medicament for treating type II diabetes.

In another aspect, the present invention provides a use of a pharmaceutical formulation comprising about 0.5% dapagliflozin or dapagliflozin (S) propylene glycol hydrate; about 70.5% metformin hydrochloride; about 5.5% hydroxypropyl cellulose; about 20.5% microcrystalline cellulose; about 5% sodium starch glycolate; and about 1% magnesium stearate; for preparing, or for the manufacture of, a medicament for treating type II diabetes.

In another aspect, the present invention provides a use of a pharmaceutical formulation comprising about 0.5% dapagliflozin or dapagliflozin (S) propylene glycol hydrate; about 75.5% metformin hydrochloride; about 6% hydroxypropyl cellulose; about 12.5% microcrystalline cellulose; about 5% sodium starch glycolate; and about 0.6% magnesium stearate; for preparing, or for the manufacture of, a medicament for treating type II diabetes.

In another aspect, the present invention provides a use of a pharmaceutical formulation comprising about 0.5% dapagliflozin or dapagliflozin (S) propylene glycol hydrate; about 77% metformin hydrochloride; about 10% hydroxypropyl cellulose; about 5% microcrystalline cellulose; about 7.5% sodium starch glycolate; and about 0.6% magnesium stearate; for preparing, or for the manufacture of, a medicament for treating type II diabetes.

In another aspect, the present invention provides a use of a pharmaceutical formulation comprising about 0.8% dapagliflozin or dapagliflozin (S) propylene glycol hydrate; about 69% metformin hydrochloride; about 3% hydroxypropyl cellulose; about 20% microcrystalline cellulose; about 6.5% hydroxypropyl cellulose, low substituted; and about 0.8% magnesium stearate; for preparing, or for the manufacture of, a medicament for treating type II diabetes.

The pharmaceutical formulations of the invention can be packaged in any packaging that facilitates stability of the drug formulation. For example, sealed high density polyethylene (HDPE) bottles containing silica gel desiccant or aluminum blister lined with PVC can be used. Use of such packaging helps to control unwanted oxidation of the product at room temperature.

The present invention also contemplates coated tablets wherein the coating comprises saxagliptin or a pharmaceutically acceptable salt thereof. Saxagliptin as the free base, as the monohydrate, or as the hydrochloride are preferred. The coated tablet comprises a tablet core, a first coating, a second coating, and optionally a third coating. The tablet core comprises metformin and an SGLT2 inhibitor. The first and second coatings optionally contain saxagliptin wherein at least one of the first and second coatings contains saxagliptin. The third coating is an optional outer protective coating. Saxagliptin, shown below, can be prepared as described in U.S. Pat. No. 6,395,767, herein incorporated by reference in its entirety for any purpose. The first and second coatings are prepared in a similar manner to the preparation of the inner seal coating layer or the middle (drug) coating layer described in WO 2005/117841, herein incorporated by reference in its entirety for any purpose. The third coating is prepared in a similar manner to the preparation of the outer protective coating layer described in WO 2005/117841.

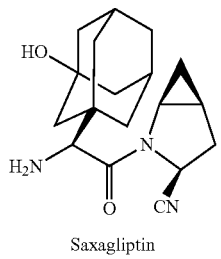 [SMILES: N#C[C@@H]1C[C@@H]2C[C@@H]2N1C(=O)[C@@H](N)C12CC3CC(CC(O)(C3)C1)C2]

Saxagliptin

The first coating includes up to 95% of polymer based on the weight of the first coating layer. The formulation will contain at least one coating layer polymer and a coating solvent, preferably the solvent is water used for processing and removed by drying. The first coating layer polymer may be hydroxypropyl methylcellulose, polyvinyl alcohol (PVA), ethyl cellulose, methacrylic polymers or hydroxypropyl cellulose, preferably PVA. The first coating optionally includes saxagliptin within the range from about 0.5 to about 70%, preferably from about 30 to about 50% by weight based on the weight of the second coating layer. The first coating may include: optionally a plasticizer such as triacetin, diethyl phthalate, tributyl sebacate or polyethylene glycol (PEG), preferably PEG; an anti-adherent or glidant such as talc, fumed silica or magnesium stearate; and an opacifying agent such as titanium dioxide. The coating layer may also include iron oxide based colorants. One coating material is commercially available under the trade name Opadry® HP or Opadry® II white.

The second coating is similar in composition to the first coating and preferably includes saxagliptin.

The third coating is similar in composition to the first coating, only without saxagliptin.

Accordingly, the present invention provides a coated tablet that comprises (1) a tablet core comprising metformin and an SGLT2 inhibitor; (2) a first coating optionally comprising saxagliptin; (3) a second coating optionally comprising saxagliptin; and (3) an optional third coating. Metformin hydrochloride is preferred and the preferred SGLT2 inhibitor is dapagliflozin or dapagliflozin (S) propylene glycol hydrate. At least one of the first and second coatings contains saxagliptin. The first and second coatings are prepared in a similar manner to the preparation of the inner seal coating layer or the middle (drug) coating layer described in WO 2005/117841. The third coating is prepared in a similar manner to the preparation of the outer protective coating layer described in WO 2005/117841.

In another aspect, the present invention provides a coated tablet wherein (1) the tablet core comprises dapagliflozin or dapagliflozin (S) propylene glycol hydrate; metformin hydrochloride; hydroxypropyl cellulose; microcrystalline cellulose; sodium starch glycolate or hydroxypropyl cellulose, low substituted; and magnesium stearate; (2) the first coating comprises a polyvinyl alcohol based polymer; (3) the second coating comprises saxagliptin and a polyvinyl alcohol based polymer; (4) and the third coating comprises a polyvinyl alcohol based polymer.

In another aspect, the present invention provides a coated tablet wherein (1) the tablet core comprises about 0.25-0.8% dapagliflozin or dapagliflozin (S) propylene glycol hydrate; about 62-77% metformin hydrochloride; about 3-10% hydroxypropyl cellulose; about 5-21% microcrystalline cellulose; about 5-9% sodium starch glycolate or about 5-8% hydroxypropyl cellulose, low substituted; and about 0.6-1.4% magnesium stearate; (2) a first coating that comprises Opadry® HP; (3) a second coating that comprises saxagliptin and Opadry® HP; and (4) a third coating that comprises Opadry® HP.

In another aspect, the present invention provides a coated tablet wherein (1) the tablet core comprises about 0.1-1% dapagliflozin or dapagliflozin (S) propylene glycol hydrate; about 60-80% metformin hydrochloride; about 1-10% hydroxypropyl cellulose; about 2-25% microcrystalline cellulose; about 4-10% sodium starch glycolate or about 3-10% hydroxypropyl cellulose, low substituted; and about 0.25-2.5% magnesium stearate; (2) a first coating that comprises Opadry® HP; (3) a second coating that comprises saxagliptin and Opadry® HP; and (4) a third coating that comprises Opadry® HP.

In another aspect, the present invention provides a coated tablet wherein (1) the tablet core comprises:

(A) about 0.5% dapagliflozin or dapagliflozin (S) propylene glycol hydrate; about 70.5% metformin hydrochloride; about 8% hydroxypropyl cellulose; about 12.5% microcrystalline cellulose; about 8% sodium starch glycolate; and about 0.6% magnesium stearate;

(B) about 0.25% dapagliflozin or dapagliflozin (S) propylene glycol hydrate; about 71% metformin hydrochloride; about 8% hydroxypropyl cellulose; about 12.5% microcrystalline cellulose; about 8% sodium starch glycolate; and about 0.6% magnesium stearate;

(C) about 0.4% dapagliflozin or dapagliflozin (S) propylene glycol hydrate; about 61.5% metformin hydrochloride; about 8% hydroxypropyl cellulose; about 21% microcrystalline cellulose; about 8.5% sodium starch glycolate; and about 1.4% magnesium stearate;

(D) about 0.4% dapagliflozin or dapagliflozin (S) propylene glycol hydrate; about 72% metformin hydrochloride; about 9% hydroxypropyl cellulose; about 12.5% microcrystalline cellulose; about 5% sodium starch glycolate; and about 1% magnesium stearate;

(E) about 0.5% dapagliflozin or dapagliflozin (S) propylene glycol hydrate; about 70.5% metformin hydrochloride; about 5.5% hydroxypropyl cellulose; about 20.5% microcrystalline cellulose; about 5% sodium starch glycolate; and about 1% magnesium stearate;

(F) about 0.5% dapagliflozin or dapagliflozin (S) propylene glycol hydrate; about 75.5% metformin hydrochloride; about 6% hydroxypropyl cellulose; about 12.5% microcrystalline cellulose; about 5% sodium starch glycolate; and about 0.6% magnesium stearate;

(G) about 0.5% dapagliflozin or dapagliflozin (S) propylene glycol hydrate; about 77% metformin hydrochloride; about 10% hydroxypropyl cellulose; about 5% microcrystalline cellulose; about 7.5% sodium starch glycolate; and about 0.6% magnesium stearate; or (H) about 0.8% dapagliflozin or dapagliflozin (S) propylene glycol hydrate; about 69% metformin hydrochloride; about 3% hydroxypropyl cellulose; about 20% microcrystalline cellulose; about 6.5% hydroxypropyl cellulose, low substituted; and about 0.8% magnesium stearate; (2) a first coating that comprises Opadry® HP; (3) a second coating that comprises saxagliptin and Opadry® HP; and (4) a third coating that comprises Opadry® HP.

Opadry® HP comprises 40% polyvinyl alcohol, 20% polyethylene glycol, 15% talc, and 25% titanium dioxide.

In another aspect, the present invention provides combination therapies that comprise the tablet of the present invention in combination with one or more: anti-diabetics; anti-hyperglycemic agents; hypolipidemic/lipid lowering agents; anti-obesity agents; anti-hypertensive agents appetite suppressants; insulin secretagogues, insulin sensitizers, glucokinase activators, glucocorticoid antagonist, fructose 1,6-bis phosphatase inhibitors, AMP kinase activators, modulators of the incretin pathway such as incretin secretagogues such as GPR119 or GPR40 agonists, incretin mimics such as Byetta, and incretin potentiators, bile acid sequestrants or bile acid receptor agonists such as TGR5 agonists, dopamine receptor agonists such as Cycloset, aldose reductase inhibitors PPARγ agonists, PPARα Agonists, PPARδ antagonists or agonists, PPARα/γ dual agonists, 11-β-HSD-1 inhibitors, dipeptidyl peptidase IV (DPP4) inhibitors other than saxagliptin, SGLT2 inhibitors other than dapagliflozin, glucagon-like peptide-1 (GLP-1), GLP-1 agonists, and PTP-1B inhibitors. Also weight loss agents acting to decreasing food intake such as sibutramine, CB1 antagonists, 5HT2C agonists, MCHR1 antagonists, and agents which decrease nutrient absorption (such as lipase inhibitors (Orlistat)), and agents which increase energy expenditure such as thyromimetics, or slow GI motility such as amylin mimetics or ghrelin antagonists.

Examples of suitable anti-diabetic agents for use in combination with the formulations of the present invention include, but are not limited to, alpha glucosidase inhibitors (acarbose or miglitol), insulins (including insulin secretagogues or insulin sensitizers), meglitinides (repaglinide), sulfonylureas (glimepiride, glyburide, gliclazide, chlorpropamide and glipizide), biguanide/glyburide combinations (Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), GPR-119 modulators, GPR 40 modulators, glucokinase inhibitors, glucagon-like peptide-1 (GLP-1) and other agonists of the GLP-1 receptor, SGLT2 inhibitors other than dapagliflozin, and dipeptidyl peptidase IV (DPP4) inhibitors other than saxagliptin.

Other suitable thiazolidinediones include, but are not limited to, MCC-555 (disclosed in U.S. Pat. No. 5,594,016, Mitsubishi), faraglitazar (GI-262570, Glaxo-Wellcome), englitazone (CP-68722, Pfizer) or darglitazone (CP-86325, Pfizer; isaglitazone, MIT/Johnson& Johnson), reglitazar (JTT-501, (JPNT/Pharmacia & Upjohn), rivoglitazone (R-119702, Sankyo/WL), liraglutide (NN-2344, Dr. Reddy/NN), and (Z)-1,4-bis-4-[(3,5-dioxo-1,2,4-oxadiazolidin-2-yl-methyl)]phenoxybut-2-ene (YM-440, Yamanouchi).

Examples of PPAR-alpha agonists, PPAR-gamma agonists and PPAR alpha/gamma dual agonists include, but are not limited to, muraglitazar, peliglitazar, tesaglitazar AR-H039242 (Astra/Zeneca), GW-501516 (Glaxo-Wellcome), KRP297 (Kyorin Merck), as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998); WO 01/21602 and in U.S. Pat. No. 6,414,002 and U.S. Pat. No. 6,653,314, the disclosures of which are incorporated herein by reference in their entireties, employing dosages as set out therein. In one embodiment, the compounds designated as preferred in the cited references are preferred for use herein.

Suitable aP2 inhibitors include, but are not limited to, those disclosed in U.S. application Ser. No. 09/391,053, filed Sep. 7, 1999, and in U.S. Pat. No. 6,548,529, the disclosures of which are incorporated herein by reference in their entireties, employing dosages as set out therein.

Suitable DPP4 inhibitors include, but are not limited to, sitagliptin and vildagliptin, as well as those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540), 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996), the compounds disclosed in U.S. application Ser. No. 10/899,641, all of which are incorporated herein by reference in their entireties, employing dosages as set out in the above references.

Suitable SGLT2 inhibitors contemplated by the present invention for combination therapies are described herein.

Suitable meglitinides include nateglinide (Novartis) or KAD1229 (PF/Kissei).

Examples of suitable anti-hyperglycemic agents for use in combination with the formulations of the present invention include, but are not limited to, glucagon-like peptide-1 (GLP-1) such as GLP-1(1-36) amide, GLP-1(7-36) amide, GLP-1 (7-37) (as disclosed in U.S. Pat. No. 5,614,492, incorporated herein by reference in its entirety), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671, incorporated herein by reference in its entirety.

Examples of suitable hypolipidemic/lipid lowering agents for use in combination with the formulations of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid co-transporter inhibitors, up-regulators of LDL receptor activity, bile acid sequestrants, cholesterol ester transfer protein (e.g., CETP inhibitors, such as torcetrapib (CP-529414, Pfizer) and JTT-705 (Akros Pharma)), PPAR agonists (as described above) and/or nicotinic acid and derivatives thereof. The hypolipidemic agent can be an up-regulator of LD2 receptor activity, such as 1(3H)-isobenzofuranone,3-(13-hydroxy-10-oxotetradecyl)-5,7-dimethoxy-(MD-700, Taisho Pharmaceutical Co. Ltd) and cholestan-3-ol,4-(2-propenyl)-(3a,4a,5a)-(LY295427, Eli Lilly). Preferred hypolipidemic agents include pravastatin, lovastatin, simvastatin, atorvastatin, fluvastatin, cerivastatin, atavastatin and rosuvastatin (ZD-4522), for example.

Examples of MTP inhibitors that can be employed as described above include, but are not limited to, those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440, all of which are incorporated herein by reference in their entireties.

Examples of HMG CoA reductase inhibitors that can be employed in combination with the formulations of the invention include, but are not limited to, mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other suitable HMG CoA reductase inhibitors that can be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, rosuvastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393,2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322. All of the cited references are incorporated herein by reference in their entireties. In addition, phosphinic acid compounds useful in inhibiting HMG CoA reductase, such as those disclosed in GB 2205837, are suitable for use in combination with the formulations of the present invention.

Examples of squalene synthetase inhibitors suitable for use herein include, but are not limited to, α-phosphono-sulfonates disclosed in U.S. Pat. No. 5,712,396, those disclosed by Biller et al., J. Med. Chem., 1988, Vol. 31, No. 10, pp. 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996). Other squalene synthetase inhibitors suitable for use herein include the terpenoid pyrophosphates disclosed by P. Ortiz de Montellano et al, J. Med. Chem., 1977, 20, 243-249; the farnesyl diphosphate analog A and presqualene pyrophosphate (PSQ-PP) analogs as disclosed by Corey and Volante, J. Am. Chem. Soc., 1976, 98, 1291-1293; phosphinylphosphonates reported by McClard, R. W. et al, J.A.C.S., 1987, 109, 5544; and cyclopropanes reported by Capson, T. L., PhD dissertation, June, 1987, Dept. Med. Chem. U of Utah, Abstract, Table of Contents, pp 16, 17, 40-43, 48-51, Summary. All of the cited references are incorporated herein by reference in their entireties.

Examples of fibric acid derivatives that can be employed in combination the formulations of the invention include, but are not limited to, fenofibrate, gemfibrozil, clofibrate, bezafibrate, ciprofibrate, clinofibrate and the like, probucol, and related compounds, as disclosed in U.S. Pat. No. 3,674,836, bile acid sequestrants, such as cholestyramine, colestipol and DEAE-Sephadex (Secholex®, Policexide), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents. In one embodiment, the fibric acid derivative is probucol or gemfibrozil. All of the cited references are incorporated herein by reference in their entireties.

Examples of ACAT inhibitors that can be employed in combination with the formulations of the invention include, but are not limited to, those disclosed in Drugs of the Future 24, 9-15 (1999), (Avasimibe); "The ACAT inhibitor, CI-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. The first water-soluble ACAT inhibitor with lipid-regulating activity. Inhibitors of acyl-CoA:cholesterol acyltransferase (ACAT). Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd). All of the cited references are incorporated herein by reference in their entireties.

Examples of suitable cholesterol absorption inhibitors for use in combination with the formulations of the invention include, but are not limited to, $SCH_{48461}$ (Schering-Plough), as well as those disclosed in Atherosclerosis 115, 45-63 (1995) and J. Med. Chem. 41, 973 (1998), incorporated herein by reference in its entirety.

Examples of suitable ileal $Na^+$/bile acid co-transporter inhibitors for use in combination with the formulations of the invention include, but are not limited to, compounds as disclosed in Drugs of the Future, 24, 425-430 (1999), incorporated herein by reference in its entirety.

Examples of lipoxygenase inhibitors that can be employed in combination with the formulations of the invention include, but are not limited to, 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al., "15-Lipoxygenase and its Inhibition: A Novel Therapeutic Target for Vascular Disease", Current Pharmaceutical Design, 1999, 5, 11-20. All of the cited references are incorporated herein by reference in their entireties.

Examples of suitable anti-hypertensive agents for use in combination with the formulations of the present invention include, but are not limited to, beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates. All of the cited references are incorporated herein by reference in their entireties.

Examples of suitable anti-obesity agents for use in combination with the formulations of the present invention include, but are not limited to, beta 3 adrenergic agonists, lipase inhibitors, serotonin (and dopamine) reuptake inhibitors, thyroid receptor beta drugs, 5HT2C agonists, (such as Arena APD-356); MCHR1 antagonists, such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, ciliary neurotrophic factors (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and anorectic agents.

Beta 3 adrenergic agonists that can be optionally employed in combination with formulations of the present invention include, but are not limited to, AJ9677 (Takeda/Dainippon), L750355 (Merck), CP331648 (Pfizer) or other known beta δ agonists, as disclosed in U.S. Pat. Nos. 5,541,204, 5,770,615, 5,491,134, 5,776,983 and 5,488,064, all of which are incorporated herein by reference in their entireties.

Examples of lipase inhibitors that can be employed in combination with formulations of the present invention include, but are not limited to, orlistat and ATL-962 (Alizyme).

Serotonin (and dopamine) reuptake inhibitors (or serotonin receptor agonists) that can be employed in combination with the formulations of the present invention include, but are not limited to, BVT-933 (Biovitrum), sibutramine, topiramate (Johnson & Johnson) and axokine (Regeneron).

Examples of thyroid receptor beta compounds that can be employed in combination with formulations of the present invention include, but are not limited to, thyroid receptor ligands, such as those disclosed in WO 97/21993 (U. Cal SF), WO 99/00353 (KaroBio) and WO 00/039077 (KaroBio), incorporated herein by reference it their entireties.

Examples of monoamine reuptake inhibitors that can be employed in combination with the formulations of the present invention include, but are not limited to, fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine and mazindol.

Anorectic agents that can be employed in combination with the formulations of the present invention include, but are not limited to, topiramate (Johnson & Johnson), dexamphetamine, phentermine, phenylpropanolamine and mazindol.

The aforementioned patents and patent applications are incorporated herein by reference.

Where any of the formulations of the invention are used in combination with other therapeutic agent(s), the other therapeutic agent(s) can be used, for example, in the amounts indicated in the Physician's Desk Reference, as in the cited patents and patent applications set out above, or as otherwise known and used by one of ordinary skill in the art.

Human Studies

In a 24-week phase 3 clinical study, the combination of metformin and an SGLT2 inhibitor dapagliflozin reduced glycosylated hemoglobin levels (HbA1c) and fasting plasma glucose (FPG) levels in type II diabetic patients. Glycosylated hemoglobin and fasting plasma glucose levels were inadequately controlled with metformin alone, as compared to placebo plus metformin. The study also showed that individuals receiving dapagliflozin had statistically greater mean reductions in body weight compared to individuals taking placebo.

The study was designed to assess the efficacy and safety of dapagliflozin as an add-on to metformin over 24 weeks in patients with inadequately controlled type 2 diabetes. The data represent findings from a randomized, double-blind, placebo-controlled study of 546 individuals with type 2 diabetes whose HbA1c was greater than or equal to 7.0 percent and less than or equal to 10 percent at baseline. After a two-week lead-in phase, individuals were randomized to one of four separate treatment arms: dapagliflozin 2.5 mg (n=137), dapagliflozin 5 mg (n=137), dapagliflozin 10 mg (n=135), or placebo (n=137). Patients in all arms also received metformin (greater than or equal to 1500 mg/d). The primary endpoint of the study compared mean HbA1c change from baseline for each dapagliflozin treatment arm compared to placebo after 24 weeks. Secondary endpoints included change from baseline in FPG and body weight at week 24 as compared to placebo, and adjusted percentage of individuals treated with dapagliflozin who achieved HbA1c of less than 7 percent at 24 weeks. Exploratory endpoints included body weight decrease of greater than or equal to 5 percent or greater than or equal to 10 percent as well as body weight percent change from baseline.

After 24 weeks, individuals receiving dapagliflozin 2.5 mg, 5 mg and 10 mg plus metformin demonstrated a statistically significant adjusted mean change in HbA1c from baseline of −0.67 percent, −0.70 percent and −0.84 percent, respectively, compared to −0.30 percent for placebo. Individuals treated with dapagliflozin demonstrated a statistically significant adjusted mean change in FPG, a secondary endpoint, from baseline at Week 24: −17.8 mg/dL for dapagliflozin 2.5 mg -21.5 mg/dL for dapagliflozin 5 mg and −23.5 mg/dL/dl for dapagliflozin 10 mg, compared to −6.0 mg/dL for placebo.

The study also evaluated the potential impact of dapagliflozin on weight loss. These findings included data measuring changes in total body weight over the 24-week study period. At 24 weeks, the change in total body weight in kg, a secondary endpoint, was −2.21 kg for dapagliflozin 2.5 mg, −3.04 kg for dapagliflozin 5 mg and −2.86 kg for dapagliflozin 10 mg, compared to −0.89 kg for placebo. Overall, more patients taking dapagliflozin achieved weight losses greater than or equal to 5 percent compared to placebo, an exploratory endpoint.

These results indicate that the combination of an SGLT2 inhibitor, in particular dapagliflozin or dapagliflozin (S)-propylene glycol hydrate, with metformin effectively treats hyperglycemia in type II diabetic patients without inducing weight gain.

EXAMPLES

The invention is illustrated further by the following examples, which are provided for illustrative purposes and are not intended to be construed as limiting the invention in scope or spirit to the specific formulations described in them.

Example 1

Hydroxypropyl cellulose SSL (HPC SSL; 229.10 g) was dissolved in 673.07 g of water in order to get a HPC-solution at 25.4%. Dapagliflozin (14.53 g) was dissolved in the solution using an over-head mixer overnight. The dapagliflozin-HPC SSL-water solution was top sprayed onto 2026.10 g of Metformin HCl (including 0.5% Magnesium stearate) in a Glatt GPCG3 fluidised bed. The granules (2090.0 g) were mixed with microcrystalline cellulose (MCC PH102; 329.65 g) and sodium starch glycolate (SSG; 210.96 g) for 5 minutes. The primary blend was final mixed with magnesium stearate (6.59 g) for 2 minutes.

Tablets were compacted at tablet weight approximately 1208 mg (tools 9.6×21 mm) using a Fette 1090 rotary tablet press. The tablets (1000 g) were coated in a Bohle BFC5 perforated tablet coating pan. The film-coating solution consisted of Opadry® II white, titanium dioxide, iron oxide yellow, iron oxide reddish-brown and water with a dry content of 21.6%. 165 g of coating solution was used and the weight gain was 3.1%.

The composition of each tablet was as follows:

| Raw material | Purpose | mg/tablet | % of composition |
|---|---|---|---|
| Metformin HCl | API | 850 | 70.39 |
| Dapagliflozin (S) PGS | API | 6.15 | 0.51 |
| HPC SSL | Binder | 96.6 | 8.0 |
| MCC PH102 | Compression aid | 150.9 | 12.5 |
| Sodium starch glycolate | Disintegrant | 96.6 | 8.0 |
| Magnesium stearate | Lubricant | 7.3 | 0.60 |

The dissolution profiles for dapagliflozin and metformin HCl tablets of Example 1 are illustrated in FIG. 1.

Example 2

Hydroxypropyl cellulose SSL (HPC SSL; 5.049 kg) was dissolved in 16.9 kg of water in order to get a HPC-solution at 23.0%. Dapagliflozin (0.3204 kg) was dissolved in the solution using an over-head mixer for at least 8 hours. The dapagliflozin-HPC SSL-water solution (11.134 kg) was top sprayed onto 22.313 kg of Metformin HCl (including 0.5% Magnesium stearate) in a Glatt GPCG30 fluidised bed. The granules were milled at 1.14 mm mesh size. The granules (23.6 kg) were mixed with microcrystalline cellulose (MCC PH102; 3.722 kg) and sodium starch glycolate (SSG; 2.383 kg) for 5 minutes. The primary blend was final mixed with magnesium stearate (0.075 kg) for 2 minutes.

Tablets were compacted at tablet weight 1208 mg (tools 9.5×20 mm) using a Fette 1200 rotary tablet press. The tablets (24.7 kg) were coated in a Glatt Coater perforated tablet coating pan. The film-coating solution consisted of Opadry® II white and water with a dry content of 20%. 4.323 kg of coating solution was used and the weight gain was 3.4%.

The composition of each tablet was as shown in Example 1. The dissolution profiles for dapagliflozin and metformin HCl tablets of Example 2 are illustrated in FIG. 1.

Example 3

Hydroxypropyl cellulose SSL (HPC SSL; 228.15 g) was dissolved in 677.15 g of water in order to get a HPC-solution at 25.2%. Dapagliflozin (7.28 g) was dissolved in the solution using an over-head mixer overnight. The dapagliflozin-HPC SSL-water solution was top sprayed onto 2026.20 g of Metformin HCl (including 0.5% Magnesium stearate) in a Glatt GPCG3 fluidised bed. The granules (2142.17 g) were mixed with microcrystalline cellulose (MCC PH102; 337.88 g) and sodium starch glycolate (SSG; 216.36 g) for 5 minutes. The primary blend was final mixed with magnesium stearate (6.74 g) for 2 minutes.

Tablets were compacted at tablet weight approximately 1203 mg (tools 9.6×21 mm) using a Fette 1090 rotary tablet press.

The composition of each tablet was as follows:

| Raw material | Purpose | mg/tablet | % of composition |
|---|---|---|---|
| Metformin HCl | API | 850 | 70.65 |
| Dapagliflozin (S) PGS | API | 3.075 | 0.25 |
| HPC SSL | Binder | 96.2 | 8.0 |
| MCC PH102 | Compression aid | 150.4 | 12.5 |
| Sodium starch glycolate | Disintegrant | 96.3 | 8.0 |
| Magnesium stearate | Lubricant | 7.3 | 0.60 |

The processing parameters for Examples 1-3 were as follows.

| Process parameter | Example 1 | Example 2 | Example 3 |
|---|---|---|---|
| Fluid bed granulation | | | |
| Inlet air temp (° C.) | 65 | 65 | 65 |
| Spray rate (g/ml) | 20 | 110-137 | 20 |
| Atomizer air pressure (bar) | 2.5 | 3.7 | 3.0 |
| Atomizer air flow (Nm³/h) | 11.2-11.4 | 14 | 13.2-13.4 |
| Fluid air flow (m³/h) | 74-98 | 400-600 | 49-95 |
| Compaction | | | |
| Tools active | 2/20 | 20/20 | 2/20 |
| Compression speed (rpm) | 55 | 45 | 66 |
| Feeder speed (rpm) | 10 | 36 | 40 |
| Compaction force (kN) | 32-38 | 39 | 38 |
| Pre-compaction force (kN) | 9.4-10.2 | 8 | 13 |
| Coating | | | |
| Inlet air volume (Nm³/h) | 150 | 500 | N/A |
| Inlet air temp (° C.) | 65 | 60 | N/A |
| Drum speed (rpm) | 15 | 11 | N/A |
| Spray rate (g/min) | 7 | 50 | N/A |
| Atomizer air pressure (bar) | 2.2 | 2.4-2.5 | N/A |

Examples 4-8

General Procedure

Hydroxypropyl cellulose SSL (HPC SSL) was dissolved in order to get a HPC-solution. Dapagliflozin was dissolved/suspended in the solution using an over-head mixer overnight. The dapagliflozin-HPC SSL-water solution was top sprayed onto Metformin HCl (including 0.5% Magnesium stearate) in a Glatt GPCG3 fluidised bed. The granules were mixed with microcrystalline cellulose (MCC PH102) and sodium starch glycolate (SSG) for 5 minutes. The primary blend was final mixed with magnesium stearate for 2 minutes. Tablets were compacted (tools 8.5×17 mm) using a Korsch XL 100 rotary tablet press.

The processing parameters for Examples 4-8 were as follows:

| Process parameter | Examples 4-8 |
|---|---|
| Fluid bed granulation | |
| Inlet air temp (° C.) | 60 |
| Spray rate (g/min) | 20 |
| Atomizer air pressure (bar) | 2.5 |
| Compaction | |
| Tools active | 3/10 |
| Compression speed (rpm) | 20 |
| Compaction force (kN) | approx. 23 |

Example 4

The composition of each tablet was as follows:

| Raw material | Purpose | mg/tablet | % of composition |
|---|---|---|---|
| Metformin HCl | API | 500 | 61.2 |
| Dapagliflozin (S) PGS | API | 3.075 | 0.4 |
| HPC SSL | Binder | 62.9 | 7.7 |
| MCC PH102 | Compression aid | 170.8 | 20.9 |
| Sodium starch glycolate | Disintegrant | 67.8 | 8.3 |
| Magnesium stearate | Lubricant | 11.4 | 1.4 |

Example 5

The composition of each tablet was as follows:

| Raw material | Purpose | mg/tablet | % of composition |
|---|---|---|---|
| Metformin HCl | API | 500 | 72.0 |
| Dapagliflozin (S) PGS | API | 3.075 | 0.4 |
| HPC SSL | Binder | 63.2 | 9.1 |
| MCC PH102 | Compression aid | 86.1 | 12.4 |
| Sodium starch glycolate | Disintegrant | 34.7 | 5.0 |
| Magnesium stearate | Lubricant | 6.9 | 1.0 |

Example 6

The composition of each tablet was as follows:

| Raw material | Purpose | mg/tablet | % of composition |
|---|---|---|---|
| Metformin HCl | API | 500 | 70.39 |
| Dapagliflozin (S) PGS | API | 3.075 | 0.51 |
| HPC SSL | Binder | 40.0 | 5.4 |
| MCC PH102 | Compression aid | 151.7 | 20.5 |
| Sodium starch glycolate | Disintegrant | 37.7 | 5.1 |
| Magnesium stearate | Lubricant | 7.4 | 1.0 |

Example 7

The composition of each tablet was as follows:

| Raw material | Purpose | mg/tablet | % of composition |
|---|---|---|---|
| Metformin HCl | API | 500 | 75.4 |
| Dapagliflozin (S) PGS | API | 3.075 | 0.5 |
| HPC SSL | Binder | 39.8 | 6.0 |
| MCC PH102 | Compression aid | 82.9 | 12.5 |
| Sodium starch glycolate | Disintegrant | 33.2 | 5.0 |
| Magnesium stearate | Lubricant | 4.0 | 0.6 |

Example 8

The composition of each tablet was as follows:

| Raw material | Purpose | mg/tablet | % of composition |
|---|---|---|---|
| Metformin HCl | API | 500 | 76.9 |
| Dapagliflozin (S) PGS | API | 3.075 | 0.5 |
| HPC SSL | Binder | 63.1 | 9.7 |
| MCC PH102 | Compression aid | 30.6 | 4.7 |
| Sodium starch glycolate | Disintegrant | 49.4 | 7.6 |
| Magnesium stearate | Lubricant | 3.9 | 0.6 |

Example 9

Hydroxypropyl cellulose SSL (HPC SSL) was dissolved in order to get a HPC-solution. Dapagliflozin was dissolved/suspended in the solution using an over-head mixer overnight. The dapagliflozin-HPC SSL-water solution/suspension was top sprayed onto Metformin HCl (including 0.5% Magnesium stearate) and L-HPC in a Glatt GPCG1 fluidised bed. The granules were mixed with microcrystalline cellulose (MCC PH102) and L-HPC for 6 minutes. The primary blend was final mixed with magnesium stearate for 2 minutes. Tablets were compacted (tools 8.5×17 mm) using a Korsch XL 100 rotary tablet press.

The processing parameters were as follows:

| Process parameter | Example 9 |
|---|---|
| Fluid bed granulation | |
| Inlet air temp (° C.) | 70 |
| Atomizer air pressure (bar) | 2.5 |
| Compaction | |
| Tools active | 3/10 |
| Compression speed (rpm) | 20 |
| Compaction force (kN) | approx. 22 |

The composition of each tablet was as follows:

| Raw material | Purpose | mg/tablet | % of composition |
|---|---|---|---|
| Metformin HCl | API | 500 | 68.9 |
| Dapagliflozin (S) PGS | API | 6.15 | 0.8 |
| HPC SSL | Binder | 21.8 | 3.0 |
| MCC PH102 | Compression aid | 145.2 | 20.0 |
| L-HPC LH21 | Disintegrant | 47.2 | 6.5 |
| Magnesium stearate | Lubricant | 5.4 | 0.8 |

Example 10

Comparative Example

The composition was as follows.

| Raw material | Purpose | Mg/tablet | % of composition |
|---|---|---|---|
| Metformin HCl | API | 500 | 72.0 |
| Dapagliflozin (PG-solvate) | API | 1.5 | 0.2 |
| HPC SSL | Binder | 15.6 | 2.2 |
| MCC PH102 | Compression aid | 138.8 | 20.0 |
| L-HPC LH21 | Disintegrant | 31.2 | 4.5 |
| Magnesium stearate | Lubricant | 7.1 | 1.0 |

Batch size: 273 tablets
Metformin Granules:

53.56 g of HPC SSL was dissolved in 125 ml of water in order to get a HPC-solution. 781.55 g of Metformin HCl and 24.29 g of L-HPC were dry mixed in a Diosna P-1/6 high shear mixer. 82.33 g of the HPC solution was added to 805.84 g of the dry mix and wet massed. The wet mass was dried, on trays in a Termaks TS8265 oven, over night. The dried granules were milled in a Freund TFC-Labo oscillating mill.

Dapagliflozin Granules:

Blend 1—296.8 g of Dapagliflozin and 361.6 g of MCC were mixed in a Turbula mixer for 5 minutes.

Blend 2—296.36 g of L-HPC and 362.94 g of MCC were mixed in a Turbula mixer for 3 minutes.

Blend 3—658.4 g of blend 1 and 658.8 g of blend 2 were mixed in a Turbula mixer for 3 minutes.

Blend 4—1317.2 g of blend 3 was mixed with the remaining part, 1637.8 g, of the MCC in a Turbula mixer for 5 minutes.

Final mixing—2050 g of blend 4 was mixed with 12.3 g of Mg-stearate (charged through a 0.5 mm screen) in a Turbula mixer for 2 minutes. The final mixed granules were compressed and milled into granules using an Alexanderwerk WP 120 V Pharma roller compaction equipment.

Final Mixing and Compression

Blend 1—11.58 g of dapaglifozin granules were mixed with 15.44 g of Metformin granules in a Turbula mixer for 3 minutes.

Blend 2—27.02 g of blend 1 was mixed with 38.60 g of Metformin granules in a Turbula mixer for 3 minutes.

Blend 3—65.62 g of blend 2 was mixed with 96.80 g of Metformin granules in a Turbula mixer for 3 minutes.

Blend 4—162.41 g of blend 3 was mixed with 249.20 g of Metformin granules in a Turbula mixer for 3 minutes.

Blend 5—94.79 g of MCC and 10.55 g of L-HPC were mixed with 409.68 g of blend 4 in a Turbula mixer for 5 minutes.

Blend 6—Final mixing, 515.02 g of blend 5 was mixed with 3.24 g of Mg-stearate (charged through a 0.5 mm screen) in a Turbula mixer for 2 minutes Tablets were compacted (tools 8.5×17 mm) using a Korsch XL 100 rotary tablet press.

The processing parameters were as follows.

| Process parameter | Example 10 |
|---|---|
| Wet granulation | Diosna P-1/6 |
| Bowl size (liter) | 4 |
| Mixer speed (rpm) | 600 |
| Chopper speed (rpm) | 1500 |

-continued

| Process parameter | Example 10 |
|---|---|
| Liquid addition rate (ml/min) | 25 |
| Dry mixing time (min) | 1 |
| Wet massing time (min) | 3 |
| Drying | Termaks TS8265 |
| Drying temperature (° C.) | 55 |
| Drying time (h) | 16 |
| Milling | Freund TFC-Labo |
| Screen size (μm) | 965 |
| Mill speed (rpm) | 143 |
| Mixing | Turbula T10B |
| Mixer speed (rpm) | 32 |
| Roller Compaction | Alexanderwerk WP120 V Pharma |
| Roll diameter (mm) | 120 |
| Roll width (mm) | 25 |
| Roll type | Knurled |
| Feed screw speed (rpm) | 40 |
| Roll speed (rpm) | 5 |
| Roll pressure (bar) | 40 |
| Granulator speed (rpm) | 50 |
| Upper screen (mm) | 3.15 |
| Lower screen (mm) | 1.00 |
| Final mixing | Turbula T10B |
| Mixer speed (rpm) | 30-34 |
| Compaction | Korsch XL100 |
| Tools active | 3/10 |
| Compression speed (rpm) | 20 |
| Compaction force (kN) | approx. 23 |
| Compaction toolings (mm) | 8.5 × 17 |

Example 11

The composition was as follows.

| Raw material | Purpose | Mg/tablet | % of composition |
|---|---|---|---|
| Metformin HCl | API | 500 | 68.0 |
| Dapagliflozin (PG-solvate) | API | 3.075 | 0.4 |
| HPC SSL | Binder | 19.4 | 2.6 |
| MCC PH102 | Compression aid | 149.0 | 20.3 |
| Sodium starch glycolate | Disintegrant | 59.6 | 8.1 |
| Magnesium stearate | Lubricant | 4.4 | 0.6 |

Batch size: 700 tablets

HPC SSL was dissolved in water in order to get a HPC-solution. Dapagliflozin was dissolved/suspended in the solution using an over-head mixer over night. The dapagliflozin-HPC SSL-water solution/suspension was top sprayed onto the Metformin HCl (including 0.5% Magnesium stearate) in a Glatt GPCG3 fluidised bed.

The granules were mixed with microcrystalline cellulose and sodium starch glycolate (SSG) for 5 minutes. The primary blend was final mixed with magnesium stearate for 2 minutes. Tablets were compacted (tools 8.5×17 mm) using a Korsch XL 100 rotary tablet press.

The processing parameters were as follows:

| Process parameter | Example 11 |
|---|---|
| Fluid bed granulation | GPCG3 |
| Inlet air temp (° C.) | 60 |
| Spray rate (g/ml) | 20 |
| Atomizer air pressure (bar) | 2.5 |
| Compaction | Korsch XL 100 |
| Tools active | 3/10 |
| Compression speed (rpm) | 20 |
| Compaction force (kN) | approx. 23 |

Example 12

The composition was as follows.

| Raw material | Purpose | Mg/tablet | % of composition |
|---|---|---|---|
| Metformin HCl | API | 1000 | 70.7 |
| Dapagliflozin (PG-solvate) | API | 3.075 | 0.2 |
| HPC SSL | Binder | 113 | 8.0 |
| MCC PH102 | Compression aid | 177 | 12.5 |
| Sodium starch glycolate | Disintegrant | 113 | 8.0 |
| Magnesium stearate | Lubricant | 9 | 0.6 |

Batch Size 27.4 Kg

Hydroxypropyl cellulose SSL (HPC SSL) (6.861 kg) was dispersed in water (23.0 kg) at 50° C. As the temperature decreased below cloud point the HPC dissolved (approx time 3 h). Dapagliflozin (0.186 kg) was added to the HPC solution at 30° C. and was dissolved during approx 2.5 h. The liquid was prepared in a jacketed vessel and the preparation time was in total less than 6 h. The liquid was left over night and used as granulation liquid the next day. The dapagliflozin-HPC SSL-water solution (12.16 kg) was top sprayed onto Metformin HCl (including 0.5% Magnesium stearate) (24.571 kg) in a Glatt GPCG30 fluidised bed. The granules were milled (1.14 mm) (25.0 kg) and mixed with microcrystalline cellulose (MCC PH102) (3.944 kg) and sodium starch glycolate (SSG) (2.525 kg) for 5 minutes. The primary blend was final mixed with magnesium stearate (0.079 kg) for 2 minutes. Tablets were compacted (tools 10.5×21.5 mm) using a Fette 1200 rotary tablet press. Some of the tablets (1.201 kg) were coated in a perforated tablet coating pan. The film-coating solution consisted of Opadry® II orange and water with a dry content of 20.0%. 216 g of coating solution was used and the weight gain was 3.5%.

The processing parameters were as follows:

| Process parameter | Example 12 |
|---|---|
| Fluid bed granulation | GPCG30 |
| Inlet air temp (° C.) | 65 |
| Spray rate (g/min) | 160 |
| Atomizer air pressure (bar) | 3.7 |
| Compaction | Fette 1200 |
| Tools active | 20/20 |
| Compression speed (rpm) | 45 |
| Pre-compaction force (kN) | approx. 9 |
| Compaction force (kN) | approx. 42 |

The dissolution profiles for dapagliflozin and metformin were as follows (n=6):

| | Dissoln. % 10 min | Dissoln. % 20 min | Dissoln. % 30 min | Dissoln. % 45 min | Dissoln. % 75 min |
|---|---|---|---|---|---|
| Dapagliflozin | 38 | 78 | 96 | 99 | 99 |
| Metformin | 41 | 80 | 97 | 100 | 100 |

Example 13

Batch Size: 27.4 Kg

Hydroxypropyl cellulose SSL (HPC SSL) (6.861 kg) was dispersed in water (23.0 kg) at 55° C. As the temperature decreased below cloud point the HPC dissolved (approx time 1 h). Dapagliflozin (0.186 kg) was added to the HPC solution at 40° C. and was dissolved during approx 3.5 h. The liquid was prepared in a jacketed vessel and the preparation time was in total less than 5 h. The liquid was left over night and used as granulation liquid the next day. The dapagliflozin-HPC SSL-water solution (12.2 kg) was top sprayed onto Metformin HCl (including 0.5% Magnesium stearate) (24.571 kg) in a Glatt GPCG30 fluidised bed. The granules were milled (1.14 mm) (25.0 kg) and mixed with microcrystalline cellulose (MCC PH102) (3.944 kg) and sodium starch glycolate (SSG) (2.524 kg) for 5 minutes. The primary blend was final mixed with magnesium stearate (0.079 kg) for 2 minutes. Tablets were compacted (tools 10.5×21.5 mm) using a Fette 1200 rotary tablet press. Some of the tablets (1.201 kg) were coated in a perforated tablet coating pan. The film-coating solution consisted of Opadry® II orange and water with a dry content of 20.0%. 216 g of coating solution was used and the weight gain was 3.2%.

The composition was as follows:

| Raw material | Purpose | Mg/tablet | % of composition |
|---|---|---|---|
| Metformin HCl | API | 1000 | 70.7 |
| Dapagliflozin (PG-solvate) | API | 3.075 | 0.2 |
| HPC SSL | Binder | 113 | 8.0 |
| MCC PH102 | Compression aid | 177 | 12.5 |
| Sodium starch glycolate | Disintegrant | 113 | 8.0 |
| Magnesium stearate | Lubricant | 9 | 0.6 |

The processing parameters were as follows.

| Process parameter | Example 13 |
|---|---|
| Fluid bed granulation | GPCG30 |
| Inlet air temp (° C.) | 65 |
| Spray rate (g/min) | 160-170 |
| Atomizer air pressure (bar) | 3.7 |
| Compaction | Fette 1200 |
| Tools active | 20/20 |
| Compression speed (rpm) | 45 |
| Pre-compaction force (kN) | approx. 9 |
| Compaction force (kN) | approx. 42 |

The dissolution profiles for dapagliflozin and metformin were as follows (n=6):

| | Dissolution % 10 min | Dissolution % 20 min | Dissolution % 30 min | Dissolution % 45 min | Dissoln % 75 min |
|---|---|---|---|---|---|
| Dapagliflozin | 37 | 77 | 95 | 97 | 97 |
| Metformin | 41 | 81 | 98 | 100 | 100 |

Example 14

Batch Size: 2.2 Kg

Dapagliflozin (12.07 g) was dispersed in water (1487.19 g) at 46° c. immediately followed by addition of hydroxypropyl cellulose SSL (HPC SSL) (444.20 g). The mixture was stirred by a lightning mixer for 30 min. The temperature was kept at 46° C. After 30 min the heating was turned off and the stirring was decreased and a few minutes later turned off. The mixture was cooled in a water bath and as the temperature decreased below cloud point the HPC dissolved. The preparation time was in total less than 3 h and the granulation liquid was used for granulation immediately. The dapagliflozin-HPC SSL-water solution (971.83 g) was top sprayed onto Metformin HCl (including 0.5% Magnesium stearate) (1971.9 g) in a Glatt GPCG3 fluidised bed. The granules (770.03 g) were mixed with microcrystalline cellulose (MCC PH102) (121.43 g) and sodium starch glycolate (SSG) (77.28 g) for 5 minutes. The primary blend was final mixed with magnesium stearate (2.43 g) for 2 minutes. Tablets were compacted (tools 10.5× 21.5 mm) using a Korsch XL 100 rotary tablet press.

The composition was as follows.

| Raw material | Purpose | Mg/tablet | % of composition |
|---|---|---|---|
| Metformin HCl | API | 1000 | 70.7 |
| Dapagliflozin (PG-solvate) | API | 3.075 | 0.2 |
| HPC SSL | Binder | 113 | 8.0 |
| MCC PH102 | Compression aid | 177 | 12.5 |
| Sodium starch glycolate | Disintegrant | 113 | 8.0 |
| Magnesium stearate | Lubricant | 9 | 0.6 |

The processing parameters were as follows.

| Process parameter | Example 14 |
|---|---|
| Fluid bed granulation | GPCG3 |
| Inlet air temp (° C.) | 65 |
| Spray rate (g/min) | 20 |
| Atomizer air pressure (bar) | 2.5 |
| Compaction | Korsch XL100 |
| Tools active | 2/8 |
| Compression speed (rpm) | 20 |
| Compaction force (kN) | approx. 36 |

Figure 2:
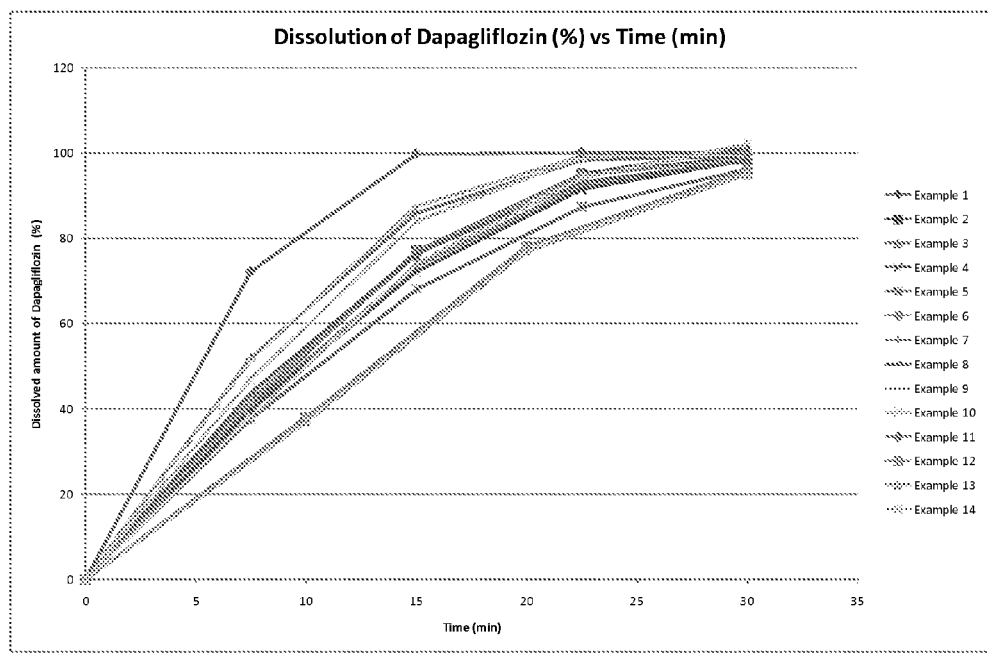
FIG. 2 describes a dissolution profile for the immediate release formulations of examples 1-14.

The dissolution profile of dapagliflozin in Examples 1 to 14 is illustrated in FIG. 2.

Content Uniformity (CU) Measurements:

CU was measured by one of the following two methods as specified for each example in Table 1 by indicating the ones where infinity testing (2) was used:

1. Each of a number of tablets (6-10 units) was dissolved in a separate flask and analyzed using HPLC (High Performance Liquid Chromatography). The relative standard deviation in percent (% RSD) was calculated on the obtained results, or
2. After having completed the dissolution measurements (3-6 units) as described below, the paddle stirring speed was increased to 250 rpm in each vessel for 15 minutes (infinity testing). After 15 minutes, a sample from each vessel was withdrawn and analyzed by HPLC. The relative standard deviation in percent (% RSD) was calculated on the obtained results.

Acceptance criterion was set to % RSD less than or equal to 6% of the target amount of active per tablet.

Tensile Strength (TS) Measurements:

The crushing strength of the tablets was determined by the diametral compression method using a Holland C50 equipment. The crushing strength was then divided by the tablet break area to obtain the TS value.

Disintegration Measurements:
The disintegration of the tablets was performed according to USP. Each tablet was placed in a tube of a basket. A 1000 ml beaker with water at 37±2° C. was used.

Dissolution Measurements:
The dissolution of the API was analysed by a USP II (paddle) method. Each tablet was placed in 1000 ml of phosphate buffer pH 6.8 at 37° C. and 75 rpm paddle speed.

TABLE 1

Content uniformity, tensile strength and disintegration for Examples 1-14.

| Example | Content uniformity of Dapa (% RSD, n = tablets tested) | Tensile strength (MPa, CP$^a$) | Disintegration time (minutes, n = tablets tested) |
|---|---|---|---|
| 1 | NA | 2.03, 255 | approx. 15$^c$, n = 3 |
| 2 | 1.0, n = 10 | 1.92, 246 | 15-16, n = 3 |
| 3 | 0.6, n = 3$^b$ | 1.96, 204 | 16, n = 3 |
| 4 | 0.5, n = 3$^b$ | 2.31, 204 | 17-18, n = 6 |
| 5 | 0.8, n = 3$^b$ | 2.13, 204 | 15-17, n = 6 |
| 6 | 1.6, n = 3$^b$ | 2.27, 199 | 13-15, n = 6 |
| 7 | 0.5, n = 3$^b$ | 2.02, 201 | 10-11, n = 6 |
| 8 | 0.6, n = 3$^b$ | 1.96, 209 | 12-13, n = 6 |
| 9 | 0.5, n = 3$^b$ | 1.87, 193 | approx. 12, n = 3 |
| 10 | 7.6, n = 6$^b$ | 1.44, 202 | 11-12, n = 3 |
| 11 | 0.7, n = 3$^b$ | 1.80, 205 | 7-8, n = 6 |
| 12 | 0.7, n = 10 | 1.97, 231 | approx. 17$^c$, n = 3 |
| 13 | 0.6, n = 10 | 1.87, 231 | approx. 16$^c$, n = 3 |
| 14 | 0.5, n = 5$^b$ | 2.18, 200 | approx. 17, n = 6 |

$^a$CP = Compaction Pressure (MPa);
$^b$Infinity testing;
$^c$Coated tablets

These results demonstrate the improved content uniformity and tensile strength of Examples 1-9 and 11-14 with respect to comparative Example 10.

We claim:

1. A pharmaceutical formulation comprising: about 0.1-2% dapagliflozin or dapagliflozin (S) propylene glycol hydrate; about 55-85% metformin hydrochloride; about 1-15% hydroxypropyl cellulose; about 2-25% microcrystalline cellulose; about 1-12% sodium starch glycolate or about 3-10% hydroxypropyl cellulose, low substituted; about 0.25-5% magnesium stearate and optionally a coating; wherein the pharmaceutical formulation is an immediate release formulation and wherein the formulation is in the form of a tablet.

2. The pharmaceutical formulation according to claim 1 wherein the formulation is about 0.25-0.8% dapagliflozin or dapagliflozin (S) propylene glycol hydrate; about 62-77% metformin hydrochloride; about 3-10% hydroxypropyl cellulose; about 5-21% microcrystalline cellulose; about 5-9% sodium starch glycolate or about 5-8% hydroxypropyl cellulose, low substituted; and about 0.6-1.4% magnesium stearate.

3. A pharmaceutical combination that comprises a pharmaceutical formulation according to claim 1 and an anti-diabetic, wherein the anti-diabetic is a sulfonylurea, thiazolidinedione, alpha glucosidase inhibitor, meglitinide, glucagon-like peptide (GLP) agonist, insulin, amylin agonist, fructose 1,6-bis phosphatase inhibitor, insulin secretagogue, insulin sensitizer, glucokinase activator, glucocorticoid antagonist, adenosine monophosphate protein (AMP) kinase activator, incretin secretagogue, incretin mimic, incretin potentiator, G protein-coupled bile acid receptor (TGR5) agonist, dopamine receptor agonist, aldose reductase inhibitor, peroxisome proliferator-activated receptor (PPAR)γ agonist, PPARα agonist, PPARδ antagonist or agonist, PPARα/γ dual agonist, 11-beta-hydroxysteroid dehydrogenase type I (11-β-HSD-1) inhibitor, dipeptidyl peptidase IV (DPP4) inhibitor other than saxagliptin, sodium-glucose transporter-2 (SGLT2) inhibitor other than dapagliflozin, glucagon-like peptide-1 (GLP-1), GLP-1 agonist, or protein-tyrosine phosphatase 1B (PTP-1B) inhibitor.

4. A pharmaceutical combination that comprises a pharmaceutical formulation according to claim 1 and a weight loss agent, wherein the weight loss agent is sibutramine, a cannabinoid receptor 1 (CB1) antagonist, a 5-hydroxytryptamine receptor 2C (5HT2C) agonist, a melanin-concentrating hormone receptor 1 (MCHR1) antagonist, Orlistat, a thyromimetic, an amylin mimetic, or a ghrelin antagonist.

5. The pharmaceutical formulation according to claim 1 wherein the formulation is about 0.1-1% dapagliflozin or dapagliflozin (S) propylene glycol hydrate; about 60-80% metformin hydrochloride; about 1-10% hydroxypropyl cellulose; about 2-25% microcrystalline cellulose; about 4-10% sodium starch glycolate or about 3-10% hydroxypropyl cellulose, low substituted; and about 0.25-2.5% magnesium stearate.

6. The pharmaceutical formulation according to claim 5 wherein the formulation is:
(A) about 0.5% dapagliflozin or dapagliflozin (S) propylene glycol hydrate; about 70.5% metformin hydrochloride; about 8% hydroxypropyl cellulose; about 12.5% microcrystalline cellulose; about 8% sodium starch glycolate; and about 0.6% magnesium stearate;
(B) about 0.25% dapagliflozin or dapagliflozin (S) propylene glycol hydrate; about 71% metformin hydrochloride; about 8% hydroxypropyl cellulose; about 12.5% microcrystalline cellulose; about 8% sodium starch glycolate; and about 0.6% magnesium stearate;
(C) about 0.4% dapagliflozin or dapagliflozin (S) propylene glycol hydrate; about 61.5% metformin hydrochloride; about 8% hydroxypropyl cellulose; about 21% microcrystalline cellulose; about 8.5% sodium starch glycolate; and about 1.4% magnesium stearate;
(D) about 0.4% dapagliflozin or dapagliflozin (S) propylene glycol hydrate; about 72% metformin hydrochloride; about 9% hydroxypropyl cellulose; about 12.5% microcrystalline cellulose; about 5% sodium starch glycolate; and about 1% magnesium stearate;
(E) about 0.5% dapagliflozin or dapagliflozin (S) propylene glycol hydrate; about 70.5% metformin hydrochloride; about 5.5% hydroxypropyl cellulose; about 20.5% microcrystalline cellulose; about 5% sodium starch glycolate; and about 1% magnesium stearate;
(F) about 0.5% dapagliflozin or dapagliflozin (S) propylene glycol hydrate; about 75.5% metformin hydrochloride; about 6% hydroxypropyl cellulose; about 12.5% microcrystalline cellulose; about 5% sodium starch glycolate; and about 0.6% magnesium stearate;
(G) about 0.5% dapagliflozin or dapagliflozin (S) propylene glycol hydrate; about 77% metformin hydrochloride; about 10% hydroxypropyl cellulose; about 5% microcrystalline cellulose; about 7.5% sodium starch glycolate; and about 0.6% magnesium stearate;
(H) about 0.8% dapagliflozin or dapagliflozin (S) propylene glycol hydrate; about 69% metformin hydrochloride; about 3% hydroxypropyl cellulose; about 20% microcrystalline cellulose; about 6.5% hydroxypropyl cellulose, low substituted; and about 0.8% magnesium stearate;
(I) about 0.4% dapagliflozin or dapagliflozin (S) propylene glycol hydrate; about 68% metformin hydrochloride; about 2.6% hydroxypropyl cellulose; about 20% microcrystalline cellulose; about 8% sodium starch glycolate; and about 0.6% magnesium stearate; or (J) about 0.2% dapagliflozin or dapagliflozin (S) propylene glycol hydrate; about 70.7% metformin hydrochloride; about 8% hydroxypropyl cellulose; about 12.5% microcrystalline cellulose; about 8% sodium starch glycolate; and about 0.6% magnesium stearate.

7. The pharmaceutical formulation according to claim 6 wherein the formulation is a tablet and there is a coating selected from a white powder comprised of 10-30% titanium dioxide, 10-30% polyethylene glycol and 10-30% talc; a brown powder comprised of 5-10% titanium dioxide and 5-10% iron oxide red; an orange powder comprised of 10-30% titanium dioxide, 10-30% polyethylene glycol and 10-30% talc; and a yellow powder comprised of 10-30% titanium dioxide, 10-30% polyethylene glycol and 10-30% talc.

8. A coated tablet that comprises (1) a tablet core that comprises dapagliflozin or dapagliflozin (S) propylene glycol hydrate; metformin hydrochloride; hydroxypropyl cellulose; microcrystalline cellulose; sodium starch glycolate or hydroxypropyl cellulose, low substituted; and magnesium stearate; (2) a first coating that comprises a polyvinyl alcohol based polymer; (3) a second coating that comprises saxagliptin and a polyvinyl alcohol based polymer; (4) and a third coating that comprises a polyvinyl alcohol based polymer.

9. A pharmaceutical formulation comprising: about 2.5-6.15 mgs of dapagliflozin or dapagliflozin (S) propylene glycol hydrate; about 500-100 mgs of metformin hydrochloride; about 19-114 mgs hydroxypropyl cellulose; about 150-177 mgs microcrystalline cellulose; about 60-114 mgs sodium starch glycolate; about 4.5-9 mgs magnesium stearate; and optionally a coating; wherein the pharmaceutical formulation is an immediate release formulation and wherein the formulation is in the form of a tablet.

10. The pharmaceutical formulation according to claim 9 comprising about 2.5 mgs of dapagliflozin or about 3.08 mgs of dapagliflozin (S) propylene glycol hydrate and about 500 mgs of metformin hydrochloride.

11. The pharmaceutical formulation according to claim 10 comprising about 19 mgs hydroxypropyl cellulose; about 150 mgs microcrystalline cellulose; about 60 mgs sodium starch glycolate; and about 4.5 mgs magnesium stearate.

12. The pharmaceutical formulation according to claim 9 comprising about 2.5 mgs of dapagliflozin or about 3.08 mgs of dapagliflozin (S) propylene glycol hydrate, and about 850 mgs of metformin hydrochloride.

13. The pharmaceutical formulation according to claim 12 comprising about 96 mgs hydroxypropyl cellulose; about 150 mgs microcrystalline cellulose; about 96 mgs sodium starch glycolate; and about 7 mgs magnesium stearate.

14. The pharmaceutical formulation according to claim 13 wherein there is a coating that is a white powder comprised of 10-30% titanium dioxide, 10-30% polyethylene glycol and 10-30% talc.

15. The pharmaceutical formulation according to claim 9 comprising about 5 mgs of dapagliflozin or about 6.15 mgs of dapagliflozin (S) propylene glycol hydrate and about 850 mgs of metformin hydrochloride.

16. The pharmaceutical formulation according to claim 15 comprising about 97 mgs hydroxypropyl cellulose; about 151 mgs microcrystalline cellulose; about 97 mgs sodium starch glycolate; and about 7 mgs magnesium stearate.

17. The pharmaceutical formulation according to claim 16 wherein there is a coating that is a brown powder comprised of 5-10% titanium dioxide and 5-10% iron oxide red.

18. The pharmaceutical formulation according to claim 9 comprising about 2.5 mgs of dapagliflozin or about 3.08 mgs of dapagliflozin (S) propylene glycol hydrate and about 1000 mgs of metformin hydrochloride.

19. The pharmaceutical formulation according to claim 18 comprising about 113 mgs hydroxypropyl cellulose; about 177 mgs microcrystalline cellulose; about 113 mgs sodium starch glycolate; and about 9 mgs magnesium stearate.

20. The pharmaceutical formulation according to claim 19 wherein there is a coating that is an orange powder comprised of 10-30% titanium dioxide, 10-30% polyethylene glycol and 10-30% talc.

21. The pharmaceutical formulation according to claim 9 comprising about 5 mgs of dapagliflozin or about 6.15 mgs of dapagliflozin (S) propylene glycol hydrate, and about 1000 mgs of metformin hydrochloride.

22. The pharmaceutical formulation according to claim 21 comprising about 114 mgs hydroxypropyl cellulose; about 177 mgs microcrystalline cellulose; about 114 mgs sodium starch glycolate; and about 9 mgs magnesium stearate.

23. The pharmaceutical formulation according to claim 22 wherein there is a coating that is a yellow powder comprised of 10-30% titanium dioxide, 10-30% polyethylene glycol and 10-30% talc.

\* \* \* \* \*